(12) United States Patent
Yan et al.

(10) Patent No.: US 11,155,862 B2
(45) Date of Patent: Oct. 26, 2021

(54) METHOD FOR RAPIDLY CONSTRUCTING AMPLICON LIBRARY THROUGH ONE-STEP PROCESS

(71) Applicant: Genetron Health (Beijing) Co., Ltd., Beijing (CN)

(72) Inventors: Hai Yan, Beijing (CN); Sizhen Wang, Beijing (CN); Yuchen Jiao, Beijing (CN); Dayong Xu, Beijing (CN); Qiaosong Zheng, Beijing (CN); Xiao Shi, Beijing (CN)

(73) Assignee: Genetron Health (Beijing) Co., Ltd., Beijing (CN)

( * ) Notice: Subject to any disclaimer, the term of this patent is extended or adjusted under 35 U.S.C. 154(b) by 182 days.

(21) Appl. No.: 16/481,938

(22) PCT Filed: Mar. 28, 2018

(86) PCT No.: PCT/CN2018/080864
§ 371 (c)(1),
(2) Date: Jul. 30, 2019

(87) PCT Pub. No.: WO2018/184495
PCT Pub. Date: Oct. 11, 2018

(65) Prior Publication Data
US 2019/0352711 A1 Nov. 21, 2019

(30) Foreign Application Priority Data
Apr. 5, 2017 (CN) .......................... 201710218529.4

(51) Int. Cl.
*C12Q 1/6869* (2018.01)
*C12N 15/10* (2006.01)
(Continued)

(52) U.S. Cl.
CPC ....... *C12Q 1/6869* (2013.01); *C12N 15/1093* (2013.01); *C12Q 1/686* (2013.01);
(Continued)

(58) Field of Classification Search
CPC ................. C12Q 1/6869; C12Q 1/686; C12Q 2525/191; C12Q 2535/122; C12N 15/1093; C40B 50/06
See application file for complete search history.

(56) References Cited

U.S. PATENT DOCUMENTS 9,677,119 B2 * 6/2017 May ..................... C12Q 1/6806
2013/0045894 A1 * 2/2013 Frey ....................... C12Q 1/686
506/16
(Continued)

FOREIGN PATENT DOCUMENTS

CN 106906210 A 6/2017
CN 107604045 A 1/2018
(Continued)

*Primary Examiner* — Jeremy C Flinders
*Assistant Examiner* — Taryn Kimberly Wood
(74) *Attorney, Agent, or Firm* — The Webb Law Firm

(57) ABSTRACT

The present invention discloses a method for rapidly constructing amplicon library including the following steps: 1. Synthesizing a primer combination for constructing an amplicon library of a DNA sample, the primer combination of the amplicon library used to construct the DNA sample includes: a forward fusion primer designed according to the target amplicon, a reverse fusion primer designed according to the target amplicon, a forward universal primer and a reverse universal primer; 2. Constructing a PCR reaction system for the DNA sample; 3. Performing PCR. The method according to the present invention can be used to construct an amplicon library in a simple and rapid manner, and since a barcode is introduced before the start of PCR, the
(Continued)

possibility of cross-contamination between the sample and the library is greatly reduced.

15 Claims, 2 Drawing Sheets

Specification includes a Sequence Listing.

(51) Int. Cl.
    *C12Q 1/686*     (2018.01)
    *C40B 50/06*     (2006.01)

(52) U.S. Cl.
    CPC . *C12Q 2525/191* (2013.01); *C12Q 2535/122* (2013.01); *C40B 50/06* (2013.01)

(56) References Cited

U.S. PATENT DOCUMENTS

| | | |
|---|---|---|
| 2016/0098516 A1 | 4/2016 | Kim et al. |
| 2016/0265065 A1* | 9/2016 | Bandla .................. A61P 43/00 |

FOREIGN PATENT DOCUMENTS

| | | |
|---|---|---|
| GN | 106319064 A | 1/2017 |
| GN | 106834286 A | 6/2017 |
| GN | 106835292 A | 6/2017 |
| WO | 2016049638 A1 | 3/2016 |

* cited by examiner

METHOD FOR RAPIDLY CONSTRUCTING AMPLICON LIBRARY THROUGH ONE-STEP PROCESS

CROSS-REFERENCE TO RELATED APPLICATIONS

This application is the United States national phase of International Application No. PCT/CN2018/080864 filed Mar. 28, 2018, and claims priority to Chinese Patent Application No. 201710218529.4 filed Apr. 5, 2017, the disclosures of which are hereby incorporated by reference in their entirety.

The Sequence Listing associated with this application is filed in electronic format via EFS-Web and is hereby incorporated by reference into the specification in its entirety. The name of the text file containing the Sequence Listing is 1905130_ST25.txt. The size of the text file is 27,920 bytes, and the text file was created on Jul. 17, 2019.

TECHNICAL FIELD

The invention relates to a field of biotechnology, and in particular to a method for rapidly constructing amplicon library through one-step process.

BACKGROUND OF RELATED ART

Next-generation sequencing (NGS) has been widely used in disease research, diagnosis and treatment in recent years due to its high throughput, high sensitivity, and high automation. Compared with traditional detection method, NGS technology can achieve multi-gene parallel detection and save samples. Besides, it has higher sensitivity which can restore the panoramic view of tumor variation in a more realistic way. However, the traditional method for constructing an amplicon library in the Life NGS platform is cumbersome, requires PCR amplification, digestion, addition, and purification, and takes about 5 hours. Further, because of the need to open the lid in a multi-step operation, the library is easily contaminated and the library loss rate is high. In addition, in the traditional method of constructing the amplicon library, the cost of establishing a library for a single sample is relatively high, which is about 200-1000 RMB per case.

The information disclosed in background part is only intended to enhance an understanding of the general background of the invention, and should not be taken as an acknowledgement or any form of suggestion that this information forms the prior art already known to a person skilled in the art.

SUMMARY OF THE INVENTION

The object of the present invention is to provide a method for rapidly constructing an amplicon library through one-step process. The method can construct the amplicon library by one-step PCR in a simple and rapid manner, and since the barcode is introduced before the start of PCR, the possibility of cross-contamination between samples and libraries is greatly reduced, and the requirements of the experimental site partition can be simplified. The method also controls the cost of establishing a single sample library at 30 RMB per case.

To achieve the above object, the present invention provides a method for constructing an amplicon library of a DNA sample, comprising the following steps.

Step 1: synthesizing a primer combination for constructing an amplicon library of a DNA sample, the primer combination of the amplicon library that is used to construct the DNA sample includes:

a forward fusion primer that is designed according to a target amplicon. The forward fusion primer comprises a first linker sequence (Bridge sequence) and a specific forward primer sequence designed according to the target amplicon, both of which are arranged in the order of 5' to 3';

a first linker sequence (Bridge sequence) and a specific forward primer sequence designed according to the target amplicon arranged in the order of 5' to 3';

a reverse fusion primer that is designed according to the target amplicon. The reverse fusion primer comprises a second linker sequence (trP1 sequence) and a specific reverse primer sequence designed according to the target amplicon, both which are arranged in the order of 5' to 3';

a forward universal primer which comprises a third linker sequence (A sequence), a barcode sequence and a first linker sequence arranged in the order of 5' to 3'; and a reverse universal primer which comprises a universal sequence (Uni sequence) and a second linker sequence arranged in the order of 5' to 3';

Step 2: constructing a PCR reaction system for the DNA samples, and mixing the forward fusion primers designed according to the target amplicon, the reverse fusion primers designed according to the target amplicon, the forward universal primers and the reverse universal primers together, to serve as a primer combination in the PCR reaction system;

Step 3: performing PCR.

In an embodiment of the present invention, the first linker sequence comprises a sequence of SEQ ID: 1, and the nucleotide sequence of the sequence of SEQ ID: 1 is GGCATACGTCCTCGTCTA.

In an embodiment of the present invention, the second linker sequence comprises a sequence of SEQ ID: 2, and the nucleotide sequence of the sequence of SEQ ID: 2 is TCTATGGGCAGTCGGTGAT.

In an embodiment of the present invention, the third linker sequence comprises a sequence of SEQ ID: 3, and a nucleotide sequence of the sequence of SEQ ID:3 is CCATCTCATCCCTGCGTGTCTCCGACTCAG.

In an embodiment of the present invention, the universal sequence comprises a sequence of SEQ ID: 4, and a nucleotide sequence of the sequence of SEQ ID: 4 is CCACTACGCCTCCGCTTTCCTC.

In an embodiment of the present invention, in the primer combination for constructing an amplicon library of the same DNA sample, the barcode sequence in the forward universal primer is the same. In the primer combinations for constructing amplicon libraries of the different DNA samples, the barcode sequences in the forward universal primers are different. The barcode sequence corresponds to the sample. The barcode sequence is different among different samples. As long as different samples can be distinguished, the barcode sequence is not specific and its sequence can be changed.

In an embodiment of the present invention, the concentration of the forward fusion primer designed according to any one of the target amplicon, the concentration of reverse fusion primer designed according to any one of the target amplicon, the concentration of forward universal primer, and the concentration of reverse universal primer are all 100 µM.

In an embodiment of the present invention, when the number of target amplicons in the same PCR reaction is greater than 1, the forward fusion primer designed according to a target amplicon is a combination of forward fusion primers designed according to each target amplicon, the reverse fusion primer designed according to the target amplicon is a combination of reverse fusion primers designed according to each target amplicon.

In an embodiment of the present invention, the molar ratio of the forward fusion primer designed according to any one of the target amplicon to the reverse fusion primer designed according to the target amplicon is 1:1; the molar ratio of the forward universal primer to the reverse universal primer is 1:1. The specific amount of forward universal primers and reverse universal primers should be adjusted according to the number of target amplicons during PCR amplification. For example, when PCR amplification, 5 target amplicons need to be amplified and 22 target amplicons need to be amplified, the specific amount of the forward universal primer and the reverse universal primer may be different, and a specific amount of the forward universal primer and the reverse universal primer may be determined by those skilled in the art according to conventional techniques in the art.

In an embodiment of the present invention, the DNA sample is genomic DNA.

In an embodiment of the present invention, the genomic DNA is extracted from a tissue sample or a formalin-fixed and paraffin-embedded sample.

In an embodiment of the present invention, the target amplicon comprises at least one selected from the group consisting of 22 target amplicons:

Chr2:29432588-29432707 (Hg19) amplicon of the ALK gene, the sequence of which is shown in SEQ ID: 5:
TAAGGGACAAGCAGCCACACCCCATTCTTGAGGGGCTGAGGTGGAAGAG

ACAGGCCCGGAGGGGTGAGGCAGTCTTTACTCACCTGTAGATGTCTCGG

GCCATCCCGAAGTCTCCAATCTTGGCCACTCTTCCAGGGCCTGGACAGG

TCAAGAGGCAGT;

Chr2:29443616-29443730 (Hg19) amplicon of the ALK gene, the sequence of which is shown in SEQ ID: 6:
CGGAGGAAGGACTTGAGGTCTCCCCCCGCCATGAGCTCCAGCAGGATGA

ACCGGGGCAGGGATTGCAGGCTCACCCCAATGCAGCGAACAATGTTCTG

GTGGTTGAATTTGCTGCAGAGCAGAGAGGGATGTAACCAAAATTAACTG

AGCTGAGTCTGG;

Chr7:140453091-140453197 (Hg19) amplicon of the BRAF gene, the sequence of which is shown in SEQ ID: 7:
CCTCAATTCTTACCATCCACAAAATGGATCCAGACAACTGTTCAAACTG

ATGGGACCCACTCCATCGAGATTTCACTGTAGCTAGACCAAAATCACCT

ATTTTTACTGTGAGGTCTTCATGAAGAAATATATCTGAGGTGTAGTAAG

TAAAGGAAAACAGTAG;

Chr7:55241604-55241726 (Hg19) amplicon of the EGFR gene, the sequence of which isshown in SEQ ID: 8:
TGACCCTTGTCTCTGTGTTCTTGTCCCCCCCAGCTTGTGGAGCCTCTTA

CACCCAGTGGAGAAGCTCCCAACCAAGCTCTCTTGAGGATCTTGAAGGA

AACTGAATTCAAAAAGATCAAAGTGCTGGGCTCCGGTGCGTTCGGCACG

GTGTATAAGGTAAGGTCCCTGG;

Chr7:55242398-55242513 (Hg19) amplicon of the EGFR gene, the sequence of which is shown in SEQ ID: 9:
ACAATTGCCAGTTAACGTCTTCCTTCTCTCTCTGTCATAGGGACTCTGG

ATCCCAGAAGGTGAGAAAGTTAAAATTCCCGTCGCTATCAAGGAATTAA

GAGAAGCAACATCTCCGAAAGCCAACAAGGAAATCCTCGATGTGAGTTT

CTGCTTTGCTGTGT;

Chr7:55248970-55249096 (Hg19) amplicon of the EGFR gene, the sequence of which is shown in SEQ ID:10:
GAAGCCACACTGACGTGCCTCTCCCTCCCTCCAGGAAGCCTACGTGATG

GCCAGCGTGGACAACCCCCACGTGTGCCGCCTGCTGGGCATCTGCCTCA

CCTCCACCGTGCAGCTCATCACGCAGCTCATGCCCTTCGGCTGCCTCCT

GGACTATGTCCGGGAACAC;

Chr7:55259505-55259621 (Hg19) amplicon of the EGFR gene, the sequence of which is shown in SEQ ID: 11:
CCGCAGCATGTCAAGATCACAGATTTTGGGCTGGCCAAACTGCTGGGTG

CGGAAGAGAAAGAATACCATGCAGAAGGAGGCAAAGTAAGGAGGTGGCT

TTAGGTCAGCCAGCATTTTCCTGACACCAGGGACCAGGCTGCCTTCCCA

CTAGCTGTATTGTTTA;

Chr17:37880969-37881082 (Hg19) amplicon of the ERBB2 gene, the sequence of which is shown in SEQ ID: 12:
CATACCCTCTCAGCGTACCCTTGTCCCCAGGAAGCATACGTGATGGCTG

GTGTGGGCTCCCCATATGTCTCCCGCCTTCTGGGCATCTGCCTGACATC

CACGGTGCAGCTGGTGACACAGCTTATGCCCTATGGCTGCCTCTTAGAC

CATGTCCG;

Chr12:25380261-25380363 (Hg19) amplicon of the KRAS gene, the sequence of which is shown in SEQ ID: 13:
AGTCCTCATGTACTGGTCCCTCATTGCACTGTACTCCTCTTGACCTGCT

GTGTCGAGAATATCCAAGAGACAGGTTTCTCCATCAATTACTACTTGCT

TCCTGTAGGAATCCTGAGAAGGGAGAAACACAGTCTGGATTATTACAGT

GCA;

Chr12: 25398183-25398310 (Hg19) amplicon of the KRAS gene, the sequence of which is shown in SEQ ID: 14:
AAAGAATGGTCCTGCACCAGTAATATGCATATTAAAACAAGATTTACCT

CTATTGTTGGATCATATTCGTCCACAAAATGATTCTGAATTAGCTGTAT

CGTCAAGGCACTCTTGCCTACGCCACCAGCTCCAACTACCACAAGTTTA

TATTCAGTCATTTTCAGCAGGCCTT;

Chr7:116340233-116340335 (Hg19) amplicon of the MET gene, the sequence of which is shown in SEQ ID: 15:
TCGATCTGCCATGTGTGCATTCCCTATCAAATATGTCAACGACTTCTTC

AACAAGATCGTCAACAAAAACAATGTGAGATGTCTCCAGCATTTTTACG

GACCCAATCATGAGCACTGCTTTAATAGGGTAAGTCACATCAGTTCCC;

-continued

Chr7: 116411880-116412005 (Hg19) amplicon of the MET gene, the sequence of which is shown in SEQ ID: 16:
CCATGATAGCCGTCTTTAACAAGCTCTTTCTTTCTCTCTGTTTTAAGAT

CTGGGCAGTGAATTAGTTCGCTACGATGCAAGAGTACACACTCCTCATT

TGGATAGGCTTGTAAGTGCCCGAAGTGTAAGCCCAACTACAGAAATGGT

TTCAAATGAATCTGTAGACTACCGAGCT;

Chr7:116417426-116417546 (Hg19) amplicon of the MET gene, the sequence of which is shown in SEQ ID: 17:
ATGTTACGCAGTGCTAACCAAGTTCTTTCTTTTGCACAGGGCATTTTGG

TTGTGTATATCATGGGACTTTGTTGGACAATGATGGCAAGAAAATTCAC

TGTGCTGTGAAATCCTTGAACAGTAAGTGGCATTTTATTTAACCATGGA

GTATACTTTTGTGGTTTGCAAC;

Chr7: 116423399-116423499 (Hg19) amplicon of the MET gene, the sequence of which is shown in SEQ ID: 18:
CAGTCAAGGTTGCTGATTTTGGTCTTGCCAGAGACATGTATGATAAAGA

ATACTATAGTGTACACAACAAAACAGGTGCAAAGCTGCCAGTGAAGTGG

ATGGCTTTGGAAAGTCTGCAAACTCAAAAGTTTACCACCAAGTCAGATG

TG;

Chr1:115256507-115256586 (Hg19) amplicon of the NRAS gene, the sequence of which is shown in SEQ ID: 19:
TTCGCCTGTCCTCATGTATTGGTCTCTCATGGCACTGTACTCTTCTTGT

CCAGCTGTATCCAGTATGTCCAACAAACAGGTTTCACCATCTATAACCA

CTTGTTTTCTGTAAGAATCCTGGGGGTG;

Chr 1: 115258651-115258755 (Hg19) amplicon of the NRAS gene, the sequence of which is shown in SEQ ID: 20:
TGAGAGACAGGATCAGGTCAGCGGGCTACCACTGGGCCTCACCTCTATG

GTGGGATCATATTCATCTACAAAGTGGTTCTGGATTAGCTGGATTGTCA

GTGCGCTTTTCCCAACACCACCTGCTCCAACCACCACCAGTTTGTACTC

AG;

Chr3:178936056-178936179 (Hg19) amplicon of the PIK3CA gene, the sequence of which is shown in SEQ ID: 21:
GGAAAATGACAAAGAACAGCTCAAAGCAATTTCTACACGAGATCCTCTC

TCTGAAATCACTGAGCAGGAGAAAGATTTTCTATGGAGTCACAGGTAAG

TGCTAAAATGGAGATTCTCTGTTTCTTTTTCTTTATTACAGAAAAAATA

ACTGAATTTGGCTGATCTCAGCATGTT;

Chr3:178952000-178952092 (Hg19) amplicon of the PIK3CA gene, the sequence of which is shown in SEQ ID: 22:
ATGCCAGAACTACAATCTTTTGATGACATTGCATACATTCGAAAGACCC

TAGCCTTAGATAAAACTGAGCAAGAGGCTTTGGAGTATTTCATGAAACA

AATGAATGATGCACATCATGGTGGCTGGACAACAAAAATGGATTG;

Chr17:7577027-7577154 (Hg19) amplicon of the TP53 gene, the sequence of which is shown in SEQ ID: 23:
CTTCTTGTCCTGCTTGCTTACCTCGCTTAGTGCTCCCTGGGGGCAGCTC

GTGGTGAGGCTCCCCTTTCTTGCGGAGATTCTCTTCCTCTGTGCGCCGG

TCTCTCCCAGGACAGGCACAAACACGCACCTCAAAGCTGTTCCGTCCCA

GTAGATTACCACTACTCAGGATAGGAAAAGAG;

Chr17:7577507-7577613 (Hg19) amplicon of the TP53 gene, the sequence of which is shown in SEQ ID: 24:
GCAAGTGGCTCCTGACCTGGAGTCTTCCAGTGTGATGATGGTGAGGATG

GGCCTCCGGTTCATGCCGCCCATGCAGGAACTGTTACACATGTAGTTGT

AGTGGATGGTGGTACAGTCAGAGCCAACCTAGGAGATAACACAGGCCCA

AGA;

Chr17:7578182-7578298 (Hg19) amplicon of the TP53 gene, the sequence of which is shown in SEQ ID: 25:
CCCCAGTTGCAAACCAGACCTCAGGCGGCTCATAGGGCACCACCACACT

ATGTCGAAAAGTGTTTCTGTCATCCAAATACTCCACACGCAAATTTCCT

TCCACTCGGATAAGATGCTGAGGAGGGGCCAGACCTAAGAGCAATCAGT

GAGGAATCAGAGG;

Chr17:7578389-7578537 (Hg19) amplicon of the TP53 gene, the sequence of which is shown in SEQ ID: 26:
ACCATCGCTATCTGAGCAGCGCTCATGGTGGGGGCAGCGCCTCACAACC

TCCGTCATGTGCTGTGACTGCTTGTAGATGGCCATGGCGCGACGCGGG

TGCCGGGCGGGGTGTGGAATCAACCCACAGCTGCACAGGGCAGGTCTT

GGCCAGTTGGCAAAACATCTTGTTGAGGGCAGGGGAGTACTG.

In an embodiment of the present invention, the specific forward primer sequence designed according to the Chr2: 29432588-29432707 (Hg19) amplicon of the ALK gene is shown as SEQ ID: 27: ACTGCCTCTTGACCTGTCC; the specific reverse primer sequence designed according to the Chr2:29432588-29432707 (Hg19) amplicon of the ALK gene is shown as SEQ ID: 28: TAAGGGACAAGCAGC-CACAC.

In an embodiment of the present invention, the specific forward primer sequence designed according to the Chr2: 29443616-29443730 (Hg19) amplicon of ALK gene is shown as SEQ ID: 29: CCAGACTCAGCTCAGTTAAT-TTTGG; the specific reverse primer sequence designed according to the Chr2: 29443616-29443730 (Hg19) amplicon of the ALK gene is shown as SEQ ID: 30: CGGAG-GAAGGACTTGAGGT.

In an embodiment of the present invention, the specific forward primer sequence designed according to the Chr7: 140453091-140453197(Hg19) amplicon of BRAF gene is shown as SEQ ID: 31: CTACTGTTTTCCTTTACTTACTA-CACCTC; the specific reverse primer sequence designed according to the Chr7: 140453091-140453197(Hg19) amplicon of the BRAF gene is shown as SEQ ID: 32: CCTCAATTCTTACCATCCACAAAATGG.

In an embodiment of the present invention, the specific forward primer sequence designed according to the Chr7: 55241604-55241726(Hg19) amplicon of EGFR gene is shown as SEQ ID: 33: TGACCCTTGTCTCTGTGTTCTTG; the specific reverse primer sequence designed according to the Chr7: 55241604-55241726(Hg19) amplicon of the BRAF gene is shown as SEQ ID: 34: CCAGGGACCTTACCTTATACACC.

In an embodiment of the present invention, the specific forward primer sequence designed according to the Chr7: 55242398-55242513 (Hg19) amplicon of EGFR gene is shown as SEQ ID:35: ACAATTGCCAGT- TAACGTCTTCC; the specific reverse primer sequence designed according to the Chr7: 55242398-55242513 (Hg19) amplicon of the EGFR gene is shown as SEQ ID: 36: ACACAGCAAAGCAGAAACTCAC.

In an embodiment of the present invention, the specific forward primer sequence designed according to the Chr7: 55248970-55249096 (Hg19) amplicon of EGFR gene is shown as SEQ ID: 37: GAAGCCACACTGACGTGC; the specific reverse primer sequence designed according to the Chr7: 55248970-55249096 (Hg19) amplicon of the EGFR gene is shown as SEQ ID: 38: GTGTTCCCGGACATAGTCCAG.

In an embodiment of the present invention, the specific forward primer sequence designed according to the Chr7: 55259505-55259621 (Hg19) amplicon of EGFR gene is shown as SEQ ID: 39: CCGCAGCATGTCAAGATCACA; the specific reverse primer sequence designed according to the Chr7: 55259505-55259621 (Hg19) amplicon of the EGFR gene is shown as SEQ ID: 40: TAAACAATACAGCTAGTGGGAAGGC.

In an embodiment of the present invention, the specific forward primer sequence designed according to the Chr17: 37880969-37881082 (Hg19) amplicon of ERBB2 gene is shown as SEQ ID: 41: CATACCCTCTCAGCGTACCC; the specific reverse primer sequence designed according to the Chr17: 37880969-37881082 (Hg19) amplicon of the ERBB2 gene is shown as SEQ ID: 42: CGGACATGGTCTAAGAGGCAG.

In an embodiment of the present invention, the specific forward primer sequence designed according to the Chr12: 25380261-25380363 (Hg19) amplicon of KRAS gene is shown as SEQ ID: 43: TGCACTGTAATAATCCAGACTGTGT; the specific reverse primer sequence designed according to the Chr12: 25380261-25380363 (Hg19) amplicon of the KRAS gene is shown as SEQ ID: 44: AGTCCTCATGTACTGGTCCCTC.

In an embodiment of the present invention, the specific forward primer sequence designed according to the Chr12: 25398183-25398310 (Hg19) amplicon of KRAS gene is shown as SEQ ID: 45: AAGGCCTGCTGAAAATGACTGA; the specific reverse primer sequence designed according to the Chr12: 25398183-25398310 (Hg19) amplicon of the KRAS gene is shown as SEQ ID: 46: AAAGAATGGTCCTGCACCAGTA.

In an embodiment of the present invention, the specific forward primer sequence designed according to the Chr7: 116340233-116340335 (Hg19) amplicon of MET gene is shown as SEQ ID: 47: TCGATCTGCCATGTGTGCATT; the specific reverse primer sequence designed according to the Chr7: 116340233-116340335 (Hg19) amplicon of the MET gene is shown as SEQ ID: 48: GGGAACTGATGTGACTTACCCT.

In an embodiment of the present invention, the specific forward primer sequence designed according to the Chr7: 116411880-116412005 (Hg19) amplicon of MET gene is shown as SEQ ID: 49: CCATGATAGCCGTCTTTAACAAGC; the specific reverse primer sequence designed according to the Chr7: 116411880-116412005 (Hg19) amplicon of the MET gene is shown as SEQ ID: 50: AGCTCGGTAGTCTACAGATTCATTT.

In an embodiment of the present invention, the specific forward primer sequence designed according to the Chr7: 116417426-116417546 (Hg19) amplicon of MET gene is shown as SEQ ID: 51: ATGTTACGCAGTGCTAACCAAG; the specific reverse primer sequence designed according to the Chr7: 116417426-116417546 (Hg19) amplicon of the MET gene is shown as SEQ ID: 52: GTTGCAAACCACAAAAGTATACTCCA.

In an embodiment of the present invention, the specific forward primer sequence designed according to the Chr7: 116423399-116423499 (Hg19) amplicon of MET gene is shown as SEQ ID: 53: CAGTCAAGGTTGCTGATTTTGGTC; the specific reverse primer sequence designed according to the Chr7: 116423399-116423499 (Hg19) amplicon of the MET gene is shown as SEQ ID: 54: CACATCTGACTTGGTGGTAAACTT.

In an embodiment of the present invention, the specific forward primer sequence designed according to the Chr1: 115256507-115256586 (Hg19) amplicon of NRAS gene is shown as SEQ ID: 55: CACCCCCAGGATTCTTACAGAAAA; the specific reverse primer sequence designed according to the Chr1: 115256507-115256586 (Hg19) amplicon of the NRAS gene is shown as SEQ ID: 56: TTCGCCTGTCCTCATGTATTGG.

In an embodiment of the present invention, the specific forward primer sequence designed according to the Chr1: 115258651-115258755 (Hg19) amplicon of NRAS gene is shown as SEQ ID: 57: CTGAGTACAAACTGGTGGTGGT; the specific reverse primer sequence designed according to the Chr1: 115258651-115258755 (Hg19) amplicon of the NRAS gene is shown as SEQ ID: 58: TGAGAGACAGGATCAGGTCAGC.

In an embodiment of the present invention, the specific forward primer sequence designed according to the Chr3: 178936056-178936179 (Hg19) amplicon of PIK3CA gene is shown as SEQ ID: 59: GGAAAATGACAAAGAACAGCTCAAAG; the specific reverse primer sequence designed according to the Chr3: 178936056-178936179 (Hg19) amplicon of the PIK3CA gene is shown as SEQ ID: 60: AACATGCTGAGATCAGCCAAATTC.

In an embodiment of the present invention, the specific forward primer sequence designed according to the Chr3: 178952000-178952092 (Hg19) amplicon of PIK3CA gene is shown as SEQ ID: 61: ATGCCAGAACTACAATCTTTTGATGAC; the specific reverse primer sequence designed according to the Chr3: 178952000-178952092 (Hg19) amplicon of the PIK3CA gene is shown as SEQ ID: 62: CAATCCATTTTTGTTGTCCAGCC.

In an embodiment of the present invention, the specific forward primer sequence designed according to the Chr17: 7577027-7577154 (Hg19) amplicon of TP53 gene is shown as SEQ ID: 63: CTCTTTTCCTATCCTGAGTAGTGGTAATC; the specific reverse primer sequence designed according to the Chr17: 7577027-7577154 (Hg19) amplicon of the TP53 gene is shown as SEQ ID: 64: CTTCTTGTCCTGCTTGCTTACC.

In an embodiment of the present invention, the specific forward primer sequence designed according to the Chr17: 7577507-7577613 (Hg19) amplicon of TP53 gene is shown as SEQ ID: 65: TCTTGGGCCTGTGTTATCTCCTAG; the specific reverse primer sequence designed according to the Chr17: 7577507-7577613 (Hg19) amplicon of the TP53 gene is shown as SEQ ID: 66: GCAAGTGGCTCCTGACCTG.

In an embodiment of the present invention, the specific forward primer sequence designed according to the Chr17: 7578182-7578298 (Hg19) amplicon of TP53 gene is shown as SEQ ID: 67: CCTCTGATTCCTCACTGATTGCTC; the specific reverse primer sequence designed according to the Chr17: 7578182-7578298 (Hg19) amplicon of the TP53 gene is shown as SEQ ID: 68: CCCCAGTTGCAAACCAGAC.

In an embodiment of the present invention, the specific forward primer sequence designed according to the Chr17: 7578389-7578537 (Hg19) amplicon of TP53 gene is shown as SEQ ID: 69: CAGTACTCCCCTGCCCTCAA; the specific reverse primer sequence designed according to the Chr17: 7578389-7578537 (Hg19) amplicon of the TP53 gene is shown as SEQ ID: 70: ACCATCGCTATCT-GAGCAGC.

In an embodiment of the present invention, the target amplicons are the following 22 species:
Chr2:29432588-29432707 (Hg19) amplicon of the ALK gene, the sequence of which is shown in SEQ ID:5;
Chr2: 29443616-29443730 (Hg19) amplicon of the ALK gene, the sequence of which is shown in SEQ ID:6;
Chr7: 140453091-140453197(Hg19) amplicon of the BRAF gene, the sequence of which is shown in SEQ ID:7;
Chr7: 55241604-55241726(Hg19) amplicon of the EGFR gene, the sequence of which is shown in SEQ ID:8;
Chr7: 55242398-55242513 (Hg19) amplicon of the EGFR gene, the sequence of which is shown in SEQ ID:9;
Chr7: 55248970-55249096 (Hg19) amplicon of the EGFR gene, the sequence of which is shown in SEQ ID:10;
Chr7: 55259505-55259621 (Hg19) amplicon of the EGFR gene, the sequence of which is shown in SEQ ID:11;
Chr17: 37880969-37881082 (Hg19) amplicon of the ERBB2 gene, the sequence of which is shown in SEQ ID:12;
Chr12: 25380261-25380363 (Hg19) amplicon of the KRAS gene, the sequence of which is shown in SEQ ID:13;
Chr12: 25398183-25398310 (Hg19) amplicon of the KRAS gene, the sequence of which is shown in SEQ ID:14;
Chr7: 116340233-116340335 (Hg19) amplicon of the MET gene, the sequence of which is shown in SEQ ID:15;
Chr7: 116411880-116412005 (Hg19) amplicon of the MET gene, the sequence of which is shown in SEQ ID:16;
Chr7: 116417426-116417546 (Hg19) amplicon of the MET gene, the sequence of which is shown in SEQ ID:17;
Chr7: 116423399-116423499 (Hg19) amplicon of the MET gene, the sequence of which is shown in SEQ ID:18;
Chr1: 115256507-115256586 (Hg19) amplicon of the NRAS gene, the sequence of which is shown in SEQ ID:19;
Chr1: 115258651-115258755 (Hg19) amplicon of the NRAS gene, the sequence of which is shown in SEQ ID:20;
Chr3: 178936056-178936179 (Hg19) amplicon of the PIK3CA gene, the sequence of which is shown in SEQ ID:21;
Chr3: 178952000-178952092 (Hg19) amplicon of the PIK3CA gene, the sequence of which is shown in SEQ ID:22;
Chr17: 7577027-7577154 (Hg19) amplicon of the TP53 gene, the sequence of which is shown in SEQ ID:23;
Chr17: 7577507-7577613 (Hg19) amplicon of the TP53 gene, the sequence of which is shown in SEQ ID:24;
Chr17: 7578182-7578298 (Hg19) amplicon of the TP53 gene, the sequence of which is shown in SEQ ID:25; and
Chr17: 7578389-7578537 (Hg19) amplicon of the TP53 gene, the sequence of which is shown in SEQ ID:26.

In an embodiment of the present invention, the molar ratio of the combination of the forward fusion primers designed according to the above 22 target amplicons, the combination of the reverse fusion primers designed according to the above 22 target amplicons, the forward universal primer and the reverse universal primer is: 0.1-0.3: 0.1-0.3: 0.5-1: 0.5-1, for example, 0.1:0.1:0.5:0.5.

In an embodiment of the present invention, the molar ratio of the forward fusion primer designed according to the Chr2:29432588-29432707 (Hg19) amplicon of ALK gene, the forward fusion primer designed according to the Chr2: 29443616-29443730 (Hg19) amplicon of ALK gene, the forward fusion primer designed according to the Chr7: 140453091-140453197(Hg19) amplicon of BRAF gene, the forward fusion primer designed according to the Chr7: 55241604-55241726(Hg19) amplicon of EGFR gene, the forward fusion primer designed according to the Chr7: 55242398-55242513 (Hg19) amplicon of EGFR gene, the forward fusion primer designed according to the Chr7: 55248970-55249096 (Hg19) amplicon of EGFR gene, the forward fusion primer designed according to the Chr7: 55259505-55259621 (Hg19) amplicon of EGFR gene, the forward fusion primer designed according to the Chr17: 37880969-37881082 (Hg19) amplicon of ERBB2 gene; the forward fusion primer designed according to the Chr12: 25380261-25380363 (Hg19) amplicon of KRAS gene, the forward fusion primer designed according to the Chr12: 25398183-25398310 (Hg19) amplicon of KRAS gene; the forward fusion primer designed according to the Chr7: 116340233-116340335 (Hg19) amplicon of MET gene, the forward fusion primer designed according to the Chr7: 116411880-116412005 (Hg19) amplicon of MET gene, the forward fusion primer designed according to the Chr7: 116417426-116417546 (Hg19) amplicon of MET gene, the forward fusion primer designed according to the Chr7: 116423399-116423499 (Hg19) amplicon of MET gene, the forward fusion primer designed according to the Chr1: 115256507-115256586 (Hg19) amplicon of NRAS gene, the forward fusion primer designed according to the Chr1: 115258651-115258755 (Hg19) amplicon of NRAS gene, the forward fusion primer design according to the Chr3: 178936056-178936179 (Hg19) amplicon of PIK3CA gene, the forward fusion primer design according to the Chr3: 178952000-178952092 (Hg19) amplicon of PIK3CA gene, the forward fusion primer design according to the Chr17: 7577027-7577154 (Hg19) amplicon of TP53 gene, the forward fusion primer designed according to the Chr17: 7577507-7577613 (Hg19) amplicon of the TP53 gene, the forward fusion primer designed according to the Chr17: 7578182-7578298 (Hg19) amplicon of the TP53 gene, and the forward fusion primer designed according to the Chr17: 7578389-7578537 (Hg19) amplicon of the TP53 gene is: 1:2:1:4:2:1:2:4:2:2:2:2:1:4:2:2:2:2:4:2:4:2.

In an embodiment of the present invention, the PCR reaction system includes the following components:

| | |
|---|---|
| PCR master mix | 10 µl; |
| DNA sample | 1-8 µl total 20 ng; |
| Primer combination for constructing an amplicon library of the same DNA sample | 2 µl; |
| DNAase-free H2O | making up to 20 µl. |

In an embodiment of the present invention, the PCR master mix is KAPA HiFi PCR Kits 2x.

In an embodiment of the present invention, the reaction procedure for performing PCR is:

| Temperature | Time | Number of cycles |
|---|---|---|
| 98° C. | 30 s | |
| 98° C. | 10 s | 22 cycles |
| 60° C. | 90 s | |
| 72° C. | 90 s | |
| 72° C. | 10 min | |
| 4° C. | — | |

In an embodiment of the present invention, after the PCR reaction, a step of purifying the PCR amplification product is also included.

Compared with the prior art, the present invention has the following advantages:

The method disclosed in the present invention is based on the design of the PGM platform, and can effectively amplify multiple target regions (amplicons) at the same time. In the process of constructing the library, the present invention only involves one round of PCR reaction and one round of product purification steps, which greatly simplifies the experimental operation of the existing commercial kit (such as PCR process, purification step, digestion and joints, etc.) Step), and saves the construction time. The entire library construction process only takes 2.5 hours (including DNA and RNA of the same sample).

Effectively elimination of sample and library contamination is achieved. The significant simplified operation process makes the library construction process more secure and reliable, and the reduction of operation process and steps effectively eliminates the library pollution that may be caused during the library construction process.

Streamlined bioinformatics analysis process is obtained. The amplicon library obtained by the method has a single structure and reliable data, and the DNA strand composition of the obtained library is simple and clear, and the subsequent bioinformatics analysis is more simplified.

After the library is constructed, the library is only needed to be quantified by the instrument "Qubit 2.0", which eliminates quantification step by the instrument "qPCR". Therefore, the library construction time is shortened and corresponding operation steps are reduced, and the experimental errors that may be caused by the cumbersome experimental process are avoided.

DETAILED DESCRIPTION OF THE EMBODIMENTS

Figure 1:
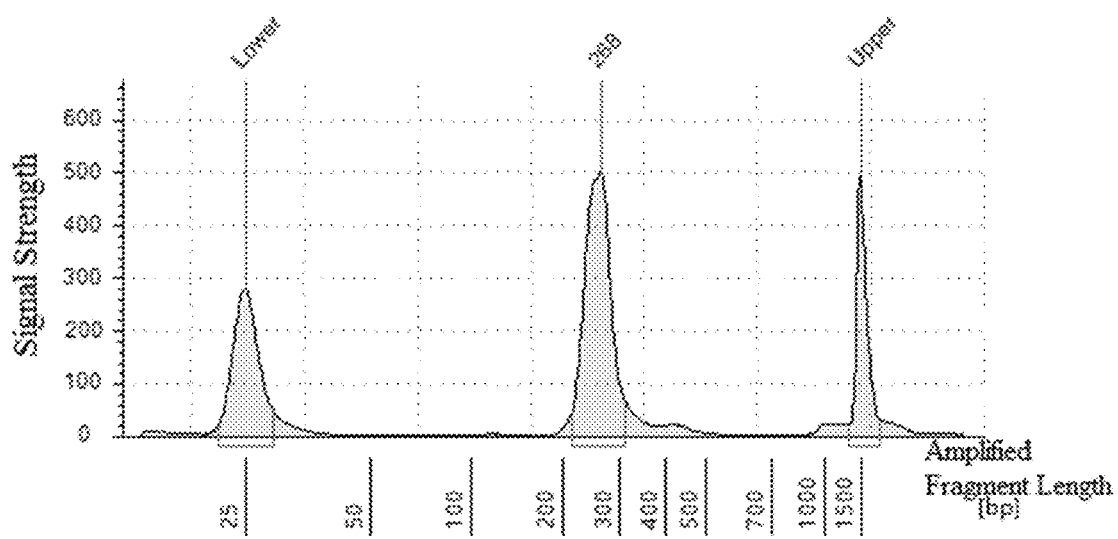
FIG. 1 is a distribution diagram of an amplification product detected after completion of construction of an amplicon library in Example 1 of the present invention.

The specific embodiments of the present invention are described in detail below with reference to the accompanying drawings, but it is understood that the scope of the present invention is not limited by the specific embodiments.

Example 1

The samples to be tested are six FFPE samples (i.e., formalin-fixed and paraffin-embedded samples, FFPE stands for Formalin-Fixed and Parrffin-Embedded), four of which are FFPE samples from patients with non-small cell lung cancer, and two are non-FFPE samples from patients without cancer. One step method is used to construct an amplicon DNA library from 6 FFPE samples using a specific designed fusion primer. The specific process is as follows:

1. Extraction of genomic DNA:

The genomic DNA in the FFPE sample is extracted using the "Qiagen FFPE DNA Kit". The detailed steps for extraction can be referred to the kit instructions. The genomic DNA is dissolved in "Tris-HCl" buffer, quality of the extracted DNA is detected using "Nano Drop". After the concentration of the sample DNA is detected using the instrument "Qubit 3.0", each genomic DNA sample is diluted to a concentration of 20 ng/μl.

2. Design and synthesize primers:

A forward fusion primer is designed according to the target amplicon. The forward fusion primer includes a first linker sequence and a specific forward primer sequence that is designed according to the target amplicon, both of which are arranged in the order of 5' to 3';

a reverse fusion primer is designed according to the target amplicon. The reverse fusion primer includes a second linker sequence and a specific reverse primer sequence designed according to the target amplicon, both of which are arranged in the order of 5' to 3';

A forward universal primer comprises a third linker sequence, barcode sequence and a first linker sequence arranged in the order of 5' to 3'; and a reverse universal primer comprises a universal sequence and a second linker sequence arranged in the order of 5' to 3'.

In the primer combination for constructing the amplicon library of the DNA sample, the information of the specific forward primer sequence and the specific reverse primer sequence designed according to the target amplicon are as follows:

Information of different target amplicons is given in the table below, and the specific forward primer sequence "Special Primer Start" and the specific reverse primer sequence "Special Primer End" designed for these amplicons are also given. Sequences of forward fusion primers designed according to the target amplicon, reverse fusion primers designed according to the target amplicon, forward universal primers, and reverse universal primers are also given. Puf represents an alternative forward universal primer and Pur represents a reverse universal primer.

| Gene/Amplicons | Chr | Amp Start | Ins Start | Ins End | Amp End | length | Primer name | Special Primer Start | Primer name | Special Primer End |
|---|---|---|---|---|---|---|---|---|---|---|
| ALK-001 | 2 | 29432569 | 29432588 | 29432707 | 29432727 | 159 | Pspf-1 | ACTGCCTCTTGACCTGTCC (SEQ ID: 27) | pspr-1 | TAAGGGACAAGCAGCCACAC (SEQ ID NO: 28) |
| ALK-002 | 2 | 29443591 | 29443616 | 29443730 | 29443749 | 159 | Pspf-2 | CCAGACTCAGCTCAGTTAATTTTG (SEQ ID: 29) | pspr-2 | CGGAGGAAGGACTTGAGGT (SEQ ID: 30) |

-continued

| Gene/Amplicons | Chr | Amp Start | Ins Start | Ins End | Amp End | length | Primer name | Special Primer Start | Primer name | Special Primer End |
|---|---|---|---|---|---|---|---|---|---|---|
| BRAF-001 | 7 | 140453062 | 140453091 | 140453197 | 140453224 | 163 | Pspf-3 | CTACTGTTTTCCTTTACTTACTACACCTC (SEQ ID: 31) | pspr-3 | CCTCAATTCTTACCATCCACAAAATGG (SEQ ID: 32) |
| EGFR-001 | 7 | 55241581 | 55241604 | 55241726 | 55241749 | 169 | Pspf-4 | TGACCCTTGTCTCTGTGTTCTTG (SEQ ID: 33) | pspr-4 | CCAGGGACCTTACCTTATACACC (SEQ ID: 34) |
| EGFR-002 | 7 | 55242375 | 55242398 | 55242513 | 55242535 | 161 | Pspf-5 | ACAATTGCCAGTTAACGTCTTCC (SEQ ID: 35) | pspr-5 | ACACAGCAAAGCAGAAACTCAC (SEQ ID: 36) |
| EGFR-003 | 7 | 55248952 | 55248970 | 55249096 | 55249117 | 166 | Pspf-6 | GAAGCCACACTGACGTGC (SEQ ID: 37) | pspr-6 | GTGTTCCCGGACATAGTCCAG (SEQ ID: 38) |
| EGFR-004 | 7 | 55259484 | 55259505 | 55259621 | 55259646 | 163 | Pspf-7 | CCGCAGCATGTCAAGATCACA (SEQ ID: 39) | pspr-7 | TAAACAATACAGCTAGTGGGAAGGC (SEQ ID: 40) |
| ERBB2-001 | 17 | 37880949 | 37880969 | 37881082 | 37881103 | 155 | Pspf-8 | CATACCCTCTCAGCGTACCC (SEQ ID: 41) | pspr-8 | CGGACATGGTCTAAGAGGCAG (SEQ ID: 42) |
| KRAS-001 | 12 | 25380236 | 25380261 | 25380363 | 25380385 | 150 | Pspf-9 | TGCACTGTAATAATCCAGACTGTGT (SEQ ID: 43) | pspr-9 | AGTCCTCATGTACTGGTCCCTC (SEQ ID: 44) |
| KRAS-002 | 12 | 25398161 | 25398183 | 25398310 | 25398332 | 172 | Pspf-10 | AAGGCCTGCTGAAAATGACTGA (SEQ ID: 45) | pspr-10 | AAAGAATGGTCCTGCACCAGTA (SEQ ID: 46) |
| MET-001 | 7 | 116340212 | 116340233 | 116340335 | 116340357 | 146 | Pspf-11 | TCGATCTGCCATGTGTGCATT (SEQ ID: 47) | pspr-11 | GGGAACTGATGTGACTTACCCT (SEQ ID: 48) |
| MET-002 | 7 | 116411856 | 116411880 | 116412005 | 116412030 | 175 | Pspf-12 | CCATGATAGCCGTCTTTAACAAGC (SEQ ID: 49) | pspr-12 | AGCTCGGTAGTCTACAGATTCATTT (SEQ ID: 50) |
| MET-003 | 7 | 116417404 | 116417426 | 116417546 | 116417572 | 169 | Pspf-13 | ATGTTACGCAGTGCTAACCAAG (SEQ ID: 51) | pspr-13 | GTTGCAAACCACAAAAGTATACTCCA (SEQ ID: 52) |
| MET-004 | 7 | 116423375 | 116423399 | 116423499 | 116423523 | 149 | Pspf-14 | CAGTCAAGGTTGCTGATTTTGGTC (SEQ ID: 53) | pspr-14 | CACATCTGACTTGGTGGTAAACTT (SEQ ID: 54) |
| NRAS-001 | 1 | 115256483 | 115256507 | 115256586 | 115256608 | 126 | Pspf-15 | CACCCCCAGGATTCTTACAGAAAA (SEQ ID: 55) | pspr-15 | TTCGCCTGTCCTCATGTATTGG (SEQ ID: 56) |
| NRAS-002 | 1 | 115258628 | 115258651 | 115258755 | 115258777 | 149 | Pspf-16 | CTGAGTACAAACTGGT | pspr-16 | TGAGAGACAGGATCAGGTCA |

-continued

| Gene/Amplicons | Chr | Amp Start | Ins Start | Ins End | Amp End | length | Primer name | Special Primer Start | Primer name | Special Primer End |
|---|---|---|---|---|---|---|---|---|---|---|
| | | 9 | | | | | | GGTGGT (SEQ ID: 57) | | GC (SEQ ID: 58) |
| PIK3CA-001 | 3 | 178936030 | 178936056 | 178936179 | 178936203 | 174 | Pspf-17 | GGAAAATGACAAAGAACAGCTCAAAG (SEQ ID: 59) | pspr-17 | AACATGCTGAGATCAGCCAAATTC (SEQ ID: 60) |
| PIK3CA-002 | 3 | 178951973 | 178952000 | 178952092 | 178952115 | 143 | Pspf-18 | ATGCCAGAACTACAATCTTTTGATGAC (SEQ ID: 61) | pspr-18 | CAATCCATTTTTGTTGTCCAGCC (SEQ ID: 62) |
| TP53-001 | 17 | 7576998 | 7577027 | 7577154 | 7577176 | 179 | Pspf-19 | CTCTTTTCCTATCCTGAGTAGTGGTAATC (SEQ ID: 63) | pspr-19 | CTTCTTGTCCTGCTTGCTTACC (SEQ ID: 64) |
| TP53-002 | 17 | 7577483 | 7577507 | 7577613 | 7577632 | 150 | Pspf-20 | TCTTGGGCCTGTGTTATCTCCTAG (SEQ ID: 65) | pspr-20 | GCAAGTGGCTCCTGACCTG (SEQ ID: 66) |
| TP53-003 | 17 | 7578158 | 7578182 | 7578298 | 7578317 | 159 | Pspf-21 | CCTCTGATTCCTCACTGATTGCTC (SEQ ID: 67) | pspr-21 | CCCCAGTTGCAAACCAGAC (SEQ ID: 68) |
| TP53-004 | 17 | 7578369 | 7578389 | 7578537 | 7578557 | 189 | Pspf-22 | CAGTACTCCCCTGCCCTCAA (SEQ ID: 69) | pspr-22 | ACCATCGCTATCTGAGCAGC (SEQ ID: 70) |

| Primer name | Primer sequence |
|---|---|
| Pspf-1 | GGCATACGTCCTCGTCTAACTGCCTCTTGACCTGTCC (SEQ ID: 71) |
| Pspf-2 | GGCATACGTCCTCGTCTACCAGACTCAGCTCAGTTAATTTTGG (SEQ ID: 72) |
| Pspf-3 | GGCATACGTCCTCGTCTACTACTGTTTTCCTTTACTTACTACACCTC (SEQ ID: 73) |
| Pspf-4 | GGCATACGTCCTCGTCTATGACCCTTGTCTCTGTGTTCTTG (SEQ ID: 74) |
| Pspf-5 | GGCATACGTCCTCGTCTAACAATTGCCAGTTAACGTCTTCC (SEQ ID: 75) |
| Pspf-6 | GGCATACGTCCTCGTCTAGAAGCCACACTGACGTGC (SEQ ID: 76) |
| Pspf-7 | GGCATACGTCCTCGTCTACCGCAGCATGTCAAGATCACA (SEQ ID: 77) |
| Pspf-8 | GGCATACGTCCTCGTCTACATACCCTCTCAGCGTACCC (SEQ ID: 78) |
| Pspf-9 | GGCATACGTCCTCGTCTATGCACTGTAATAATCCAGACTGTGT (SEQ ID: 79) |
| Pspf-10 | GGCATACGTCCTCGTCTAAAGGCCTGCTGAAAATGACTGA (SEQ ID: 80) |
| Pspf-11 | GGCATACGTCCTCGTCTATCGATCTGCCATGTGTGCATT (SEQ ID: 81) |
| Pspf-12 | GGCATACGTCCTCGTCTACCATGATAGCCGTCTTTAACAAGC (SEQ ID: 82) |
| Pspf-13 | GGCATACGTCCTCGTCTAATGTTACGCAGTGCTAACCAAG (SEQ ID: 83) |
| Pspf-14 | GGCATACGTCCTCGTCTACAGTCAAGGTTGCTGATTTTGGTC (SEQ ID: 84) |
| Pspf-15 | GGCATACGTCCTCGTCTACACCCCCAGGATTCTTACAGAAAA (SEQ ID: 85) |
| Pspf-16 | GGCATACGTCCTCGTCTACTGAGTACAAACTGGTGGTGGT (SEQ ID: 86) |
| Pspf-17 | GGCATACGTCCTCGTCTAGGAAAATGACAAAGAACAGCTCAAAG (SEQ ID: 87) |
| Pspf-18 | GGCATACGTCCTCGTCTAATGCCAGAACTACAATCTTTTGATGAC (SEQ ID: 88) |
| Pspf-19 | GGCATACGTCCTCGTCTACTCTTTTCCTATCCTGAGTAGTGGTAATC (SEQ ID: 89) |
| Pspf-20 | GGCATACGTCCTCGTCTATCTTGGGCCTGTGTTATCTCCTAG (SEQ ID: 90) |

| Primer name | Primer sequence |
|---|---|
| Pspf-21 | GGCATACGTCCTCGTCTACCTCTGATTCCTCACTGATTGCTC (SEQ ID: 91) |
| Pspf-22 | GGCATACGTCCTCGTCTACAGTACTCCCCTGCCCTCAA (SEQ ID: 92) |
| pspr-1 | TCTATGGGCAGTCGGTGATTAAGGGACAAGCAGCCACAC (SEQ ID: 93) |
| pspr-2 | TCTATGGGCAGTCGGTGATCGGAGGAAGGACTTGAGGT (SEQ ID: 94) |
| pspr-3 | TCTATGGGCAGTCGGTGATCCTCAATTCTTACCATCCACAAAATGG (SEQ ID: 95) |
| pspr-4 | TCTATGGGCAGTCGGTGATCCAGGGACCTTACCTTATACACC (SEQ ID: 96) |
| pspr-5 | TCTATGGGCAGTCGGTGATACACAGCAAAGCAGAAACTCAC (SEQ ID: 97) |
| pspr-6 | TCTATGGGCAGTCGGTGATGTGTTCCCGGACATAGTCCAG (SEQ ID: 98) |
| pspr-7 | TCTATGGGCAGTCGGTGATTAAACAATACAGCTAGTGGGAAGGC (SEQ ID: 99) |
| pspr-8 | TCTATGGGCAGTCGGTGATCGGACATGGTCTAAGAGGCAG (SEQ ID: 100) |
| pspr-9 | TCTATGGGCAGTCGGTGATAGTCCTCATGTACTGGTCCCTC (SEQ ID: 101) |
| pspr-10 | TCTATGGGCAGTCGGTGATAAAGAATGGTCCTGCACCAGTA (SEQ ID: 102) |
| pspr-11 | TCTATGGGCAGTCGGTGATGGGAACTGATGTGACTTACCCT (SEQ ID: 103) |
| pspr-12 | TCTATGGGCAGTCGGTGATAGCTCGGTAGTCTACAGATTCATTT (SEQ ID: 104) |
| pspr-13 | TCTATGGGCAGTCGGTGATGTTGCAAACCACAAAGTATACTCCA (SEQ ID: 105) |
| pspr-14 | TCTATGGGCAGTCGGTGATCACATCTGACTTGGTGGTAAACTT (SEQ ID: 106) |
| pspr-15 | TCTATGGGCAGTCGGTGATTTCGCCTGTCCTCATGTATTGG (SEQ ID: 107) |
| pspr-16 | TCTATGGGCAGTCGGTGATTGAGAGACAGGATCAGGTCAGC (SEQ ID: 108) |
| pspr-17 | TCTATGGGCAGTCGGTGATAACATGCTGAGATCAGCCAAATTC (SEQ ID: 109) |
| pspr-18 | TCTATGGGCAGTCGGTGATCAATCCATTTTTGTTGTCCAGCC (SEQ ID: 110) |
| pspr-19 | TCTATGGGCAGTCGGTGATCTTCTTGTCCTGCTTGCTTACC (SEQ ID: 111) |
| pspr-20 | TCTATGGGCAGTCGGTGATGCAAGTGGCTCCTGACCTG (SEQ ID: 112) |
| pspr-21 | TCTATGGGCAGTCGGTGATCCCCAGTTGCAAACCAGAC (SEQ ID: 113) |
| pspr-22 | TCTATGGGCAGTCGGTGATACCATCGCTATCTGAGCAGC (SEQ ID: 114) |
| puf-1 | CCATCTCATCCCTGCGTGTCTCCGACTCAGCTTGACACCGCGGCATACGTCCTCGTCTA (SEQ ID: 115) |
| puf-2 | CCATCTCATCCCTGCGTGTCTCCGACTCAGTTGGAGGCCAGCGGCATACGTCCTCGTCTA (SEQ ID: 116) |
| puf-3 | CCATCTCATCCCTGCGTGTCTCCGACTCAGTGGAGCTTCCTCGGCATACGTCCTCGTCTA (SEQ ID: 117) |
| puf-4 | CCATCTCATCCCTGCGTGTCTCCGACTCAGTCAGTCCGAACGGCATACGTCCTCGTCTA (SEQ ID: 118) |
| puf-5 | CCATCTCATCCCTGCGTGTCTCCGACTCAGTAAGGCAACCACGGCATACGTCCTCGTCTA (SEQ ID: 119) |
| puf-6 | CCATCTCATCCCTGCGTGTCTCCGACTCAGTTCTAAGAGACGGCATACGTCCTCGTCTA (SEQ ID: 120) |
| puf-7 | CCATCTCATCCCTGCGTGTCTCCGACTCAGTCCTAACATAACGGCATACGTCCTCGTCTA (SEQ ID: 121) |
| puf-8 | CCATCTCATCCCTGCGTGTCTCCGACTCAGCGGACAATGGCGGCATACGTCCTCGTCTA (SEQ ID: 122) |
| puf-9 | CCATCTCATCCCTGCGTGTCTCCGACTCAGTTGAGCCTATTCGGCATACGTCCTCGTCTA (SEQ ID: 123) |
| puf-10 | CCATCTCATCCCTGCGTGTCTCCGACTCAGCCGCATGGAACGGCATACGTCCTCGTCTA (SEQ ID: 124) |
| pur | CCACTACGCCTCCGCTTTCCTCTCTATGGGCAGTCGGTGAT (SEQ ID: 125) |

The first linker sequence is GGCATACGTCCTCGTCTA (SEQ ID: 1), the second linker sequence is TCTATGGGCAGTCGGTGAT (SEQ ID: 2), the third linker sequence is CCATCTCATCCCTGCGTGTCTCCGACTCAG (SEQ ID: 3), and the universal sequence is CCACTACGCCTCCGCTTTCCTC (SEQ ID: 4).

3. Form a PCR reaction system. The specific PCR reaction system is as follows:

| PCR reaction system component | content |
|---|---|
| KAPA HiFi PCR Kits 2x | 10 μl |
| Genomic DNA (10 ng/μl itself) | 2 μl |
| Primer combination for constructing an amplicon library of the same DNA sample | 2 μl |
| DNAase free H2O | make up to the total of 20 μl |
| Total | 20 μl |

Primer combinations for constructing an amplicon library of the same DNA sample are prepared by the following methods: (1) the forward universal primer, the reverse universal primer, and each forward fusion primer designed according to the 22 target amplicons and each reverse fusion primer are dissolved in water to a concentration of 100 μM; (2) 22 forward fusion primers with a serial number ranging from small to large are respectively mixed with a concentration of 100 μM, and the molar ratio is 1:2:1:4:2:1:2:4:2:2:2:2:4:2:2:2:2:4:2:4:2, so as to obtain the forward fusion primer combination, and 22 reverse fusion primers with a concentration of 100 μM are respectively mixed with the corresponding forward fusion primers in equal volume to obtain a reverse fusion primer combination, and then the forward fusion primer combination and the reverse fusion primer combination are mixed in equal volume; (3) mixing in equal volume of forward universal primers and reverse universal primers with concentrations of 100 µM; (4) the forward fusion primer combination, the reverse fusion primer combination, the forward universal primer and the reverse universal primer are mixed according to a molar ratio of 0.1:0.1:0.5:0.5, so that the amplicons for constructing the DNA sample are obtained. Six different sets of samples to be tested need to correspond to primer combinations containing six different barcode sequence tags.

4. Carry out the PCR program. The PCR instrument is the 2720 Thermal Cycler of Applied Bio-system. The PCR reaction procedure is as follows:

| Temperature | Time | Number of cycles |
|---|---|---|
| 98° C. | 30 s | |
| 98° C. | 10 s | 22 Cycles |
| 60° C. | 90 s | |
| 72° C. | 90 s | |
| 72° C. | 10 min | |
| 4° C. | — | |

5. After the PCR reaction, purification is carried out using "Agencourt AMPure XP Kit" (Cat. No. A63880/A63881/A63882) from Beckman Coulter company. The steps are as follows:

1) take out the Agencourt AMPure XP Kit 30 minutes in advance, rotate the magnetic beads in the Kit thoroughly, and keep the EP tube at room temperature.

2) After the completion of the PCR reaction, the magnetic beads are rotated again sufficiently, and 20 µL of magnetic beads are added to the system, repeatedly blow 5 times or more, or rotate thoroughly, and allow the Kit to be placed at room temperature for 5 minutes.

3) Transfer the EP tube to the magnetic stand and keep for 5 minutes until the solution is clarified. Carefully remove the supernatant with a pipette, taking care not to touch the beads.

4) Add 100 µL of freshly prepared 80% ethanol solution to each tube, and place the EP tube on the magnetic stand and rotate two turns, keep it for 5 minutes, and discard the supernatant.

5) Repeat step 4) once.

6) Open the EP tube and keep it at room temperature to make the liquid volatilize completely. Make sure the surfaces of the magnetic beads are dull, and be careful not to over-dry the magnetic beads.

7) Remove the EP tube from the magnetic stand, add 30 µL of PCR-grade purified water, rotate and mix, and keep it for 10 minutes at room temperature.

8) Place the EP tube on the magnetic stand for 2 minutes or until the solution is clarified. Carefully suck the supernatant from the side away from the magnet with a pipette, taking care not to touch the beads.

At this point, the amplicon library is constructed. FIG. 1 shows the distribution of amplified products detected by Agilent 2200 TapeStation Systems after the completion of the library. The abscissa is the length of the fragment, the ordinate is the signal intensity (FU), and the lower peak is the 25 bp position marker, the upper peak is a 1500 bp position marker. As shown in FIG. 1, the PCR products obtained by PCR amplification are concentrated in the range of 241-271 bp. FIG. 1 shows that the experimental results are consistent with the experimental design. From FIG. 1, the size of the constructed library and the library concentration can be judged.

6. Sequencing and results analysis

Figure 2:
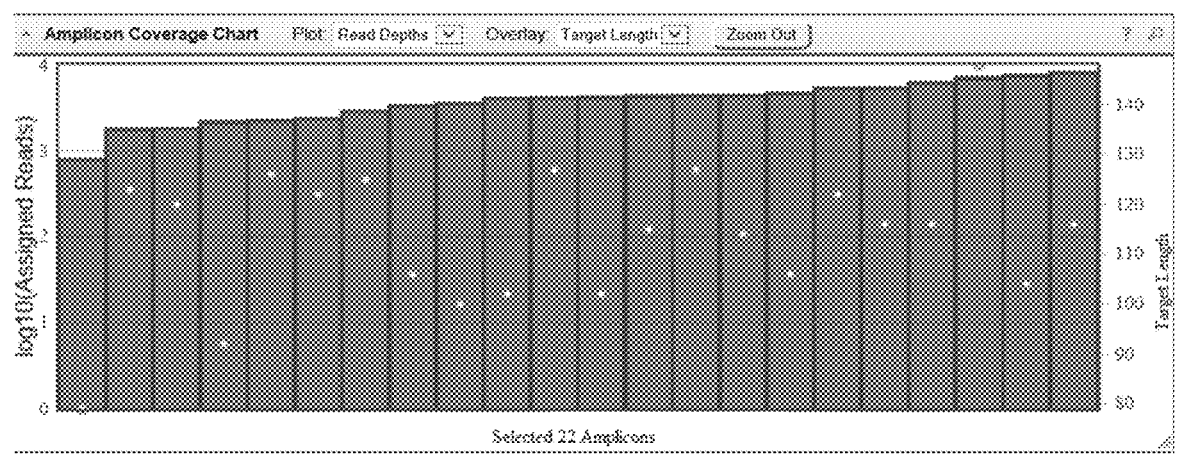
FIG. 2 is a related parameter of 22 amplicons in the library obtained in Example 1 of the present invention.

The amplicon library is obtained by the fusion primer one-step method. The amplicon sequencing is performed using the chip 318 of the Ion PGM platform, and the data amount of each library is 50 M bps. The average sequencing depth of each sample is not less than 1600X, and the single amplicon sequencing depth reached 600X. The obtained sequencing results are shown in FIG. 2. From FIG. 2, it is possible to further analyze whether or not each amplicon of the 22 amplicons is amplified and the amplification uniformity of each amplicon.

The results of sequencing are analyzed by data processing and bioinformatics analysis to obtain mutations in the detected genes. The data processing process includes conversion, quality control and sequence alignment of the sequencing data (reference genome is NCBI GRCh37/Hg19), mutation site analysis and other processes, and the mutation information of the detected samples is obtained through data processing analysis.

The actual sample collection is as follows: Among the FFPE samples of 6 subjects, no tumor-related mutations are detected in 2 normal human samples, among the 4 FFPE samples of tumor patients, p.R248W mutation is detected in Sample1, p.T790M mutation is detected in Sample2, p.G12A mutation is detected in Sample3, and p.E545K mutation is detected in Sample4. This result is consistent with the results of the sanger test. The practical applicability and good specificity of the present invention are fully illustrated.

The foregoing descriptions of specific embodiments of the present invention are presented for purposes of illustration and description. It is not intended to be exhaustive or to limit the invention to the precise form disclosed, and obviously many modifications and variations are possible in light of the above teaching. The exemplary embodiments are chosen and described in order to explain certain principles of the invention and their practical application, to thereby enable others skilled in the art to make and utilize various exemplary embodiments of the present invention, as well as various alternatives and modifications thereof. The invention is to be limited only by the claims provided below and equivalents thereof.

The invention claimed is:

1. A method for constructing an amplicon library of a DNA sample, comprising the following steps:
   1) synthesizing a primer combination which is used for constructing an amplicon library of a DNA sample, wherein the primer combination of the amplicon library used to construct the DNA sample includes:
      a forward fusion primer designed according to a target amplicon, the forward fusion primer comprising a first linker sequence (Bridge sequence) and a specific forward primer sequence designed according to the target amplicon, both of which are arranged in the order of 5' to 3';
      a reverse fusion primer designed according to the target amplicon, the reverse fusion primer comprising a second linker sequence (trP1 sequence) and a specific downstream primer sequence designed according to the target amplicon, both of which are arranged in the order of 5' to 3';
      a forward universal primer comprising a third linker sequence (A sequence), a barcode sequence and a first linker sequence arranged in the order of 5' to 3'; and
      a reverse universal primer comprising a universal sequence (Uni sequence) and a second linker sequence arranged in the order of 5' to 3';
   2) constructing a PCR reaction system for the DNA sample, and mixing the forward fusion primers designed according to the target amplicon, the reverse fusion primers designed according to the target amplicon, the forward universal primers and the reverse universal primers together, to serve as a primer combination in the PCR reaction system; and
   3) performing PCR,
   wherein the first linker sequence comprises a sequence of SEQ ID: 1, the second linker sequence comprises a sequence of SEQ ID 2, the third linker sequence comprises a sequence of SEQ ID: 3, and the universal sequence comprises a sequence of SEQ ID: 4.

2. The method for constructing an amplicon library of a DNA sample according to claim 1, wherein in a primer combination for constructing a plurality of amplicon libraries of the same DNA sample, the barcode sequences in the forward universal primers are the same; in a primer combination for constructing amplicon libraries of different DNA samples, the barcode sequences in the forward universal primers are different.

3. The method for constructing an amplicon library of a DNA sample according to claim 1, wherein when the number of target amplicons in a same PCR reaction is greater than one, the forward fusion primer designed according to the target amplicon is a combination of forward fusion primers designed according to each target amplicon, the reverse fusion primer designed according to the target amplicon is a combination of reverse fusion primers designed according to each target amplicon.

4. The method for constructing an amplicon library of a DNA sample according to claim 1, wherein the DNA sample is genomic DNA, and the genomic DNA is extracted from a tissue sample or a formalin-fixed paraffin-embedded sample.

5. The method for constructing an amplicon library of a DNA sample according to claim 1, wherein the target amplicon comprises at least one selected from the group consisting of twenty-two target amplicons:
   Chr2:29432588-29432707 (Hg19) amplicon of the ALK gene, the sequence of which is shown in SEQ ID:5;
   Chr2: 29443616-29443730 (Hg19) amplicon of the ALK gene, the sequence of which is shown in SEQ ID:6;
   Chr7: 140453091-140453197(Hg19) amplicon of the BRAF gene, the sequence of which is shown in SEQ ID:7;
   Chr7: 55241604-55241726(Hg19) amplicon of the EGFR gene, the sequence of which is shown in SEQ ID:8;
   Chr7: 55242398-55242513 (Hg19) amplicon of the EGFR gene, the sequence of which is shown in SEQ ID:9;
   Chr7: 55248970-55249096 (Hg19) amplicon of the EGFR gene, the sequence of which is shown in SEQ ID:10;
   Chr7: 55259505-55259621 (Hg19) amplicon of the EGFR gene, the sequence of which is shown in SEQ ID:11;
   Chr17: 37880969-37881082 (Hg19) amplicon of the ERBB2 gene, the sequence of which is shown in SEQ ID:12;
   Chr12: 25380261-25380363 (Hg19) amplicon of the KRAS gene, the sequence of which is shown in SEQ ID:13;

Chr12: 25398183-25398310 (Hg19) amplicon of the KRAS gene, the sequence of which is shown in SEQ ID:14;

Chr7: 116340233-116340335 (Hg19) amplicon of the MET gene, the sequence of which is shown in SEQ ID:15;

Chr7: 116411880-116412005 (Hg19) amplicon of the MET gene, the sequence of which is shown in SEQ ID:16;

Chr7: 116417426-116417546 (Hg19) amplicon of the MET gene, the sequence of which is shown in SEQ ID:17;

Chr7: 116423399-116423499 (Hg19) amplicon of the MET gene, the sequence of which is shown in SEQ ID:18;

Chr1: 115256507-115256586 (Hg19) amplicon of the NRAS gene, the sequence of which is shown in SEQ ID:19;

Chr1: 115258651-115258755 (Hg19) amplicon of the NRAS gene, the sequence of which is shown in SEQ ID:20;

Chr3: 178936056-178936179 (Hg19) amplicon of the PIK3CA gene, the sequence of which is shown in SEQ ID:21;

Chr3: 178952000-178952092 (Hg19) amplicon of the PIK3CA gene, the sequence of which is shown in SEQ ID:22;

Chr17: 7577027-7577154 (Hg19) amplicon of the TP53 gene, the sequence of which is shown in SEQ ID:23;

Chr17: 7577507-7577613 (Hg19) amplicon of the TP53 gene, the sequence of which is shown in SEQ ID:24;

Chr17: 7578182-7578298 (Hg19) amplicon of the TP53 gene, the sequence of which is shown in SEQ ID:25; and Chr17: 7578389-7578537 (Hg19) amplicon of the TP53 gene, the sequence of which is shown in SEQ ID:26.

6. The method for constructing an amplicon library of a DNA sample according to claim 5, wherein, the specific forward primer sequence designed according to the Chr2:29432588-29432707 (Hg19) amplicon of the ALK gene is shown as SEQ ID: 27; the specific reverse primer sequence designed according to the Chr2:29432588-29432707 (Hg19) amplicon of the ALK gene is shown as SEQ ID: 28;

the specific forward primer sequence designed according to the Chr2: 29443616-29443730 (Hg19) amplicon of ALK gene is shown as SEQ ID: 29; the reverse downstream primer sequence designed according to the Chr2: 29443616-29443730 (Hg19) amplicon of the ALK gene is shown as SEQ ID: 30;

the specific forward primer sequence designed according to the Chr7: 140453091-140453197(Hg19) amplicon of BRAF gene is shown as SEQ ID: 31; the specific reverse primer sequence designed according to the Chr7: 140453091-140453197(Hg19) amplicon of the EGFR gene is shown as SEQ ID: 32;

the specific forward primer sequence designed according to the Chr7: 55241604-55241726(Hg19) amplicon of EGFR gene is shown as SEQ ID: 33; the specific reverse primer sequence designed according to the Chr7: 55241604-55241726(Hg19) amplicon of the EGFR gene is shown as SEQ ID: 34.

7. The method for constructing an amplicon library of a DNA sample according to claim 1, wherein the target amplicons are the following twenty-two species:

Chr2:29432588-29432707 (Hg19) amplicon of the ALK gene, the sequence of which is shown in SEQ ID:5;

Chr2: 29443616-29443730 (Hg19) amplicon of the ALK gene, the sequence of which is shown in SEQ ID:6;

Chr7: 140453091-140453197(Hg19) amplicon of the BRAF gene, the sequence of which is shown in SEQ ID:7;

Chr7: 55241604-55241726(Hg19) amplicon of the EGFR gene, the sequence of which is shown in SEQ ID:8;

Chr7: 55242398-55242513 (Hg19) amplicon of the EGFR gene, the sequence of which is shown in SEQ ID:9;

Chr7: 55248970-55249096 (Hg19) amplicon of the EGFR gene, the sequence of which is shown in SEQ ID:10;

Chr7: 55259505-55259621 (Hg19) amplicon of the EGFR gene, the sequence of which is shown in SEQ ID:11;

Chr17: 37880969-37881082 (Hg19) amplicon of the ERBB2 gene, the sequence of which is shown in SEQ ID:12;

Chr12: 25380261-25380363 (Hg19) amplicon of the KRAS gene, the sequence of which is shown in SEQ ID:13;

Chr12: 25398183-25398310 (Hg19) amplicon of the KRAS gene, the sequence of which is shown in SEQ ID:14;

Chr7: 116340233-116340335 (Hg19) amplicon of the MET gene, the sequence of which is shown in SEQ ID:15;

Chr7: 116411880-116412005 (Hg19) amplicon of the MET gene, the sequence of which is shown in SEQ ID:16;

Chr7: 116417426-116417546 (Hg19) amplicon of the MET gene, the sequence of which is shown in SEQ ID:17;

Chr7: 116423399-116423499 (Hg19) amplicon of the MET gene, the sequence of which is shown in SEQ ID:18;

Chr1: 115256507-115256586 (Hg19) amplicon of the NRAS gene, the sequence of which is shown in SEQ ID:19;

Chr1: 115258651-115258755 (Hg19) amplicon of the NRAS gene, the sequence of which is shown in SEQ ID:20;

Chr3: 178936056-178936179 (Hg19) amplicon of the PIK3CA gene, the sequence of which is shown in SEQ ID:21;

Chr3: 178952000-178952092 (Hg19) amplicon of the PIK3CA gene, the sequence of which is shown in SEQ ID:22;

Chr17: 7577027-7577154 (Hg19) amplicon of the TP53 gene, the sequence of which is shown in SEQ ID:23;

Chr17: 7577507-7577613 (Hg19) amplicon of the TP53 gene, the sequence of which is shown in SEQ ID:24;

Chr17: 7578182-7578298 (Hg19) amplicon of the TP53 gene, the sequence of which is shown in SEQ ID:25; and Chr17: 7578389-7578537 (Hg19) amplicon of the TP53 gene, the sequence of which is shown in SEQ ID:26.

8. The method for constructing an amplicon library of a DNA sample according to claim 7, wherein the molar ratio of the combination of the forward fusion primers designed according to the twenty-two target amplicons, the combination of the reverse fusion primers designed according to the above twenty-two target amplicons, the forward universal primer and the reverse universal primer is:

0.1-0.3: 0.1-0.3: 0.5-1: 0.5-1.

9. The method for constructing an amplicon library of a DNA sample according to claim 8, wherein the PCR reaction system includes the following components:
PCR master mix, 10 µl;
DNA sample 1-8 µl total 20 ng;
Primer combination for constructing an amplicon library of the same DNA sample 2 µl;
DNAase-free H₂O making up to 20 µl.

10. The method for constructing an amplicon library of a DNA sample according to claim 5, wherein,
the specific forward primer sequence designed according to the Chr7: 55242398-55242513 (Hg19) amplicon of EGFR gene is shown as SEQ ID:35; the specific reverse primer sequence designed according to the Chr7: 55242398-55242513 (Hg19) amplicon of the EGFR gene is shown as SEQ ID: 36;
the specific forward primer sequence designed according to the Chr7: 55248970-55249096 (Hg19) amplicon of EGFR gene is shown as SEQ ID: 37; the specific reverse primer sequence designed according to the Chr7: 55248970-55249096 (Hg19) amplicon of the EGFR gene is shown as SEQ ID: 38;
the specific forward primer sequence designed according to the Chr7: 55259505-55259621 (Hg19) amplicon of EGFR gene is shown as SEQ ID: 39; the specific reverse primer sequence designed according to the Chr7: 55259505-55259621 (Hg19) amplicon of the EGFR gene is shown as SEQ ID: 40.

11. The method for constructing an amplicon library of a DNA sample according to claim 5, wherein,
the specific forward primer sequence designed according to the Chr17: 37880969-37881082 (Hg19) amplicon of ERBB2 gene is shown as SEQ ID: 41; the specific reverse primer sequence designed according to the Chr17: 37880969-37881082 (Hg19) amplicon of the ERBB2 gene is shown as SEQ ID: 42;
the specific forward primer sequence designed according to the Chr12: 25380261-25380363 (Hg19) amplicon of KRAS gene is shown as SEQ ID: 43; the specific reverse primer sequence designed according to the Chr12: 25380261-25380363 (Hg19) amplicon of the KRAS gene is shown as SEQ ID: 44;
the specific forward primer sequence designed according to the Chr12: 25398183-25398310 (Hg19) amplicon of KRAS gene is shown as SEQ ID: 45; the specific reverse primer sequence designed according to the Chr12: 25398183-25398310 (Hg19) amplicon of the KRAS gene is shown as SEQ ID: 46.

12. The method for constructing an amplicon library of a DNA sample according to claim 5, wherein,
the specific forward primer sequence designed according to the Chr7: 116340233-116340335 (Hg19) amplicon of MET gene is shown as SEQ ID: 47; the specific reverse primer sequence designed according to the Chr7: 116340233-116340335 (Hg19) amplicon of the MET gene is shown as SEQ ID: 48;
the specific forward primer sequence designed according to the Chr7: 116411880-116412005 (Hg19) amplicon of MET gene is shown as SEQ ID: 49; the specific reverse primer sequence designed according to the Chr7: 116411880-116412005 (Hg19) amplicon of the MET gene is shown as SEQ ID: 50;
the specific forward primer sequence designed according to the Chr7: 116417426-116417546 (Hg19) amplicon of MET gene is shown as SEQ ID: 51; the specific reverse primer sequence designed according to the Chr7: 116417426-116417546 (Hg19) amplicon of the MET gene is shown as SEQ ID: 52.

13. The method for constructing an amplicon library of a DNA sample according to claim 5, wherein,
the specific forward primer sequence designed according to the Chr7: 116423399-116423499 (Hg19) amplicon of MET gene is shown as SEQ ID: 53; the specific reverse primer sequence designed according to the Chr7: 116423399-116423499 (Hg19) amplicon of the MET gene is shown as SEQ ID: 54;
the specific forward primer sequence designed according to the Chr1: 115256507-115256586 (Hg19) amplicon of NRAS gene is shown as SEQ ID: 55; the specific reverse primer sequence designed according to the Chr1: 115256507-115256586 (Hg19) amplicon of the NRAS gene is shown as SEQ ID: 56;
the specific forward primer sequence designed according to the Chr1: 115258651-115258755 (Hg19) amplicon of NRAS gene is shown as SEQ ID: 57; the specific reverse primer sequence designed according to the Chr1: 115258651-115258755 (Hg19) amplicon of the NRAS gene is shown as SEQ ID: 58.

14. The method for constructing an amplicon library of a DNA sample according to claim 5, wherein,
the specific forward primer sequence designed according to the Chr3: 178936056-178936179 (Hg19) amplicon of PIK3CA gene is shown as SEQ ID: 59; the specific reverse primer sequence designed according to the Chr3: 178936056-178936179 (Hg19) amplicon of the PIK3CA gene is shown as SEQ ID: 60;
the specific forward primer sequence designed according to the Chr3: 178952000-178952092 (Hg19) amplicon of PIK3CA gene is shown as SEQ ID: 61; the specific reverse primer sequence designed according to the Chr3: 178952000-178952092 (Hg19) amplicon of the PIK3CA gene is shown as SEQ ID: 62;
the specific forward primer sequence designed according to the Chr17: 7577027-7577154 (Hg19) amplicon of TP53 gene is shown as SEQ ID: 63; the specific reverse primer sequence designed according to the Chr17: 7577027-7577154 (Hg19) amplicon of the TP53 gene is shown as SEQ ID: 64.

15. The method for constructing an amplicon library of a DNA sample according to claim 5, wherein,
the specific forward primer sequence designed according to the Chr17: 7577507-7577613 (Hg19) amplicon of TP53 gene is shown as SEQ ID: 65; the specific reverse primer sequence designed according to the Chr17: 7577507-7577613 (Hg19) amplicon of the TP53 gene is shown as SEQ ID: 66;
the specific forward primer sequence designed according to the Chr17: 7578182-7578298 (Hg19) amplicon of TP53 gene is shown as SEQ ID: 67; the specific reverse primer sequence designed according to the Chr17: 7578182-7578298 (Hg19) amplicon of the TP53 gene is shown as SEQ ID: 68;
the specific forward primer sequence designed according to the Chr17: 7578389-7578537 (Hg19) amplicon of TP53 gene is shown as SEQ ID: 69; the specific reverse primer sequence designed according to the Chr17: 7578389-7578537 (Hg19) amplicon of the TP53 gene is shown as SEQ ID: 70.

* * * * *

SEQUENCE LISTING

<160> NUMBER OF SEQ ID NOS: 125

<210> SEQ ID NO 1
<211> LENGTH: 18
<212> TYPE: DNA
<213> ORGANISM: Artificial Sequence
<220> FEATURE:
<223> OTHER INFORMATION: linker sequence

<400> SEQUENCE: 1
ggcatacgtc ctcgtcta                                              18

<210> SEQ ID NO 2
<211> LENGTH: 19
<212> TYPE: DNA
<213> ORGANISM: Artificial Sequence
<220> FEATURE:
<223> OTHER INFORMATION: linker sequence

<400> SEQUENCE: 2
tctatgggca gtcggtgat                                             19

<210> SEQ ID NO 3
<211> LENGTH: 30
<212> TYPE: DNA
<213> ORGANISM: Artificial Sequence
<220> FEATURE:
<223> OTHER INFORMATION: linker sequence

<400> SEQUENCE: 3
ccatctcatc cctgcgtgtc tccgactcag                                 30

<210> SEQ ID NO 4
<211> LENGTH: 22
<212> TYPE: DNA
<213> ORGANISM: Artificial Sequence
<220> FEATURE:
<223> OTHER INFORMATION: universal sequence

<400> SEQUENCE: 4
ccactacgcc tccgctttcc tc                                         22

<210> SEQ ID NO 5
<211> LENGTH: 159
<212> TYPE: DNA
<213> ORGANISM: Artificial Sequence
<220> FEATURE:
<223> OTHER INFORMATION: Chr2:29432588-29432707 (Hg19) amplicon of the
     ALK gene

<400> SEQUENCE: 5
taagggacaa gcagccacac cccattcttg aggggctgag gtggaagaga caggcccgga    60
ggggtgaggc agtctttact cacctgtaga tgtctcgggc catcccgaag tctccaatct   120
tggccactct tccagggcct ggacaggtca agaggcagt                          159

<210> SEQ ID NO 6
<211> LENGTH: 159
<212> TYPE: DNA
<213> ORGANISM: Artificial Sequence
<220> FEATURE:
<223> OTHER INFORMATION: Chr2: 29443616-29443730 (Hg19) amplicon of the
     ALK gene

<400> SEQUENCE: 6
cggaggaagg acttgaggtc tcccccccgcc atgagctcca gcaggatgaa ccggggcagg    60
gattgcaggc tcaccccaat gcagcgaaca atgttctggt ggttgaattt gctgcagagc   120
agagagggat gtaaccaaaa ttaactgagc tgagtctgg                          159

<210> SEQ ID NO 7
<211> LENGTH: 163
<212> TYPE: DNA
<213> ORGANISM: Artificial Sequence
<220> FEATURE:

<223> OTHER INFORMATION: Chr7: 140453091-140453197 amplicon of the BRAF
      gene

<400> SEQUENCE: 7
cctcaattct taccatccac aaaatggatc cagacaactg ttcaaactga tgggacccac    60
tccatcgaga tttcactgta gctagaccaa aatcacctat ttttactgtg aggtcttcat   120
gaagaaatat atctgaggtg tagtaagtaa aggaaaacag tag                     163

<210> SEQ ID NO 8
<211> LENGTH: 169
<212> TYPE: DNA
<213> ORGANISM: Artificial Sequence
<220> FEATURE:
<223> OTHER INFORMATION: Chr7: 55241604-55241726 amplicon of the EGFR
      gene

<400> SEQUENCE: 8
tgacccttgt ctctgtgttc ttgtcccccc cagcttgtgg agcctcttac acccagtgga    60
gaagctccca accaagctct cttgaggatc ttgaaggaaa ctgaattcaa aaagatcaaa   120
gtgctgggct ccggtgcgtt cggcacggtg tataaggtaa ggtccctgg              169

<210> SEQ ID NO 9
<211> LENGTH: 161
<212> TYPE: DNA
<213> ORGANISM: Artificial Sequence
<220> FEATURE:
<223> OTHER INFORMATION: Chr7: 55242398-55242513 amplicon of the EGFR
      gene

<400> SEQUENCE: 9
acaattgcca gttaacgtct tccttctctc tctgtcatag ggactctgga tcccagaagg    60
tgagaaagtt aaaattcccg tcgctatcaa ggaattaaga gaagcaacat ctccgaaagc   120
caacaaggaa atcctcgatg tgagtttctg ctttgctgtg t                       161

<210> SEQ ID NO 10
<211> LENGTH: 166
<212> TYPE: DNA
<213> ORGANISM: Artificial Sequence
<220> FEATURE:
<223> OTHER INFORMATION: Chr7: 55248970-55249096 amplicon of the EGFR
      gene

<400> SEQUENCE: 10
gaagccacac tgacgtgcct ctccctccct ccaggaagcc tacgtgatgg ccagcgtgga    60 caaccccac gtgtgccgcc tgctgggcat ctgcctcacc tccaccgtgc agctcatcac    120
gcagctcatg cccttcggct gcctcctgga ctatgtccgg aacac                   166

<210> SEQ ID NO 11
<211> LENGTH: 163
<212> TYPE: DNA
<213> ORGANISM: Artificial Sequence
<220> FEATURE:
<223> OTHER INFORMATION: Chr7: 55259505-55259621 amplicon of the EGFR
      gene

<400> SEQUENCE: 11
ccgcagcatg tcaagatcac agattttggg ctggccaaac tgctgggtgc ggaagagaaa    60
gaataccatg cagaaggagg caaagtaagg aggtggcttt aggtcagcca gcattttcct   120
gacaccaggg accaggctgc cttcccacta gctgtattgt tta                     163

<210> SEQ ID NO 12
<211> LENGTH: 155
<212> TYPE: DNA
<213> ORGANISM: Artificial Sequence
<220> FEATURE:
<223> OTHER INFORMATION: Chr17: 37880969-37881082 amplicon of the ERBB2
      gene

<400> SEQUENCE: 12
cataccctct cagcgtaccc ttgtccccag gaagcatacg tgatggctgg tgtgggctcc     60
ccatatgtct cccgccttct gggcatctgc ctgacatcca cggtgcagct ggtgacacag    120
cttatgccct atggctgcct cttagaccat gtccg                               155

<210> SEQ ID NO 13
<211> LENGTH: 150
<212> TYPE: DNA
<213> ORGANISM: Artificial Sequence
<220> FEATURE:
<223> OTHER INFORMATION: Chr12: 25380261-25380363 amplicon of the KRAS
      gene

<400> SEQUENCE: 13
agtcctcatg tactggtccc tcattgcact gtactcctct tgacctgctg tgtcgagaat     60
atccaagaga caggtttctc catcaattac tacttgcttc ctgtaggaat cctgagaagg    120
gagaaacaca gtctggatta ttacagtgca                                     150

<210> SEQ ID NO 14
<211> LENGTH: 172
<212> TYPE: DNA
<213> ORGANISM: Artificial Sequence
<220> FEATURE:
<223> OTHER INFORMATION: Chr12: 25398183-25398310 amplicon of the KRAS
      gene

<400> SEQUENCE: 14
aaagaatggt cctgcaccag taatatgcat attaaaacaa gatttacctc tattgttgga     60
tcatattcgt ccacaaaatg attctgaatt agctgtatcg tcaaggcact cttgcctacg    120
ccaccagctc caactaccac aagtttatat tcagtcattt tcagcaggcc tt            172

<210> SEQ ID NO 15
<211> LENGTH: 146
<212> TYPE: DNA
<213> ORGANISM: Artificial Sequence
<220> FEATURE:
<223> OTHER INFORMATION: Chr7: 116340233-116340335 amplicon of the MET
      gene

<400> SEQUENCE: 15
tcgatctgcc atgtgtgcat tccctatcaa atatgtcaac gacttcttca acaagatcgt     60
caacaaaaac aatgtgagat gtctccagca tttttacgga cccaatcatg agcactgctt    120
taatagggta agtcacatca gttccc                                         146

<210> SEQ ID NO 16
<211> LENGTH: 175
<212> TYPE: DNA
<213> ORGANISM: Artificial Sequence
<220> FEATURE:
<223> OTHER INFORMATION: Chr7: 116411880-116412005 amplicon of the MET
      gene

<400> SEQUENCE: 16

```
ccatgatagc cgtcttttaac aagctctttc tttctctctg ttttaagatc tgggcagtga      60
attagttcgc tacgatgcaa gagtacacac tcctcatttg gataggcttg taagtgcccg     120
aagtgtaagc ccaactacag aaatggtttc aaatgaatct gtagactacc gagct          175

<210> SEQ ID NO 17
<211> LENGTH: 169
<212> TYPE: DNA
<213> ORGANISM: Artificial Sequence
<220> FEATURE:
<223> OTHER INFORMATION: Chr7: 116417426-116417546 amplicon of the MET
      gene

<400> SEQUENCE: 17
atgttacgca gtgctaacca agttctttct tttgcacagg gcattttggt tgtgtatatc      60
atgggacttt gttggacaat gatggcaaga aaattcactg tgctgtgaaa tccttgaaca     120
gtaagtggca ttttatttaa ccatggagta tactttgtg gtttgcaac                  169

<210> SEQ ID NO 18
<211> LENGTH: 149
<212> TYPE: DNA
<213> ORGANISM: Artificial Sequence
<220> FEATURE:
<223> OTHER INFORMATION: Chr7: 116423399-116423499 amplicon of the MET
      gene

<400> SEQUENCE: 18
cagtcaaggt tgctgatttt ggtcttgcca gagacatgta tgataaagaa tactatagtg      60
tacacaacaa aacaggtgca aagctgccag tgaagtggat ggctttggaa agtctgcaaa     120
ctcaaaagtt taccaccaag tcagatgtg                                       149

<210> SEQ ID NO 19
<211> LENGTH: 126
<212> TYPE: DNA
<213> ORGANISM: Artificial Sequence
<220> FEATURE:
<223> OTHER INFORMATION: Chr1: 115256507-115256586 amplicon of the NRAS
      gene

<400> SEQUENCE: 19
ttcgcctgtc ctcatgtatt ggtctctcat ggcactgtac tcttcttgtc cagctgtatc      60
cagtatgtcc aacaaacagg tttcaccatc tataaccact tgttttctgt aagaatcctg     120
ggggtg                                                                126

<210> SEQ ID NO 20
<211> LENGTH: 149
<212> TYPE: DNA
<213> ORGANISM: Artificial Sequence
<220> FEATURE:
<223> OTHER INFORMATION: Chr1: 115258651-115258755 amplicon of the NRAS
      gene

<400> SEQUENCE: 20
tgagagacag gatcaggtca gcgggctacc actgggcctc acctctatgg tgggatcata      60
ttcatctaca aagtggttct ggattagctg gattgtcagt gcgcttttcc caacaccacc     120
tgctccaacc accaccagtt tgtactcag                                       149

<210> SEQ ID NO 21
<211> LENGTH: 174
<212> TYPE: DNA
<213> ORGANISM: Artificial Sequence
```

<220> FEATURE:
<223> OTHER INFORMATION: Chr3: 178936056-178936179 amplicon of the
      PIK3CA gene

<400> SEQUENCE: 21

| ggaaaatgac aaagaacagc tcaaagcaat ttctacacga gatcctctct ctgaaatcac | 60 |
| tgagcaggag aaagattttc tatggagtca caggtaagtg ctaaaatgga gattctctgt | 120 |
| ttcttttct ttattacaga aaaaataact gaatttggct gatctcagca tgtt | 174 |

<210> SEQ ID NO 22
<211> LENGTH: 143
<212> TYPE: DNA
<213> ORGANISM: Artificial Sequence
<220> FEATURE:
<223> OTHER INFORMATION: Chr3: 178952000-178952092 amplicon of the
      PIK3CA gene

<400> SEQUENCE: 22

| atgccagaac tacaatcttt tgatgacatt gcatacattc gaaagaccct agccttagat | 60 |
| aaaactgagc aagaggcttt ggagtatttc atgaaacaaa tgaatgatgc acatcatggt | 120 |
| ggctggacaa caaaaatgga ttg | 143 |

<210> SEQ ID NO 23
<211> LENGTH: 179
<212> TYPE: DNA
<213> ORGANISM: Artificial Sequence
<220> FEATURE:
<223> OTHER INFORMATION: Chr17: 7577027-7577154 amplicon of the TP53
      gene

<400> SEQUENCE: 23

| cttcttgtcc tgcttgctta cctcgcttag tgctccctgg gggcagctcg tggtgaggct | 60 |
| cccctttctt gcggagattc tcttcctctg tgcgccggtc tctcccagga caggcacaaa | 120 |
| cacgcacctc aaagctgttc cgtcccagta gattaccact actcaggata ggaaaagag | 179 |

<210> SEQ ID NO 24
<211> LENGTH: 150
<212> TYPE: DNA
<213> ORGANISM: Artificial Sequence
<220> FEATURE:
<223> OTHER INFORMATION: Chr17: 7577507-7577613 amplicon of the TP53
      gene

<400> SEQUENCE: 24

| gcaagtggct cctgacctgg agtcttccag tgtgatgatg gtgaggatgg gcctccggtt | 60 |
| catgccgccc atgcaggaac tgttacacat gtagttgtag tggatggtgg tacagtcaga | 120 |
| gccaacctag gagataacac aggcccaaga | 150 |

<210> SEQ ID NO 25
<211> LENGTH: 160
<212> TYPE: DNA
<213> ORGANISM: Artificial Sequence
<220> FEATURE:
<223> OTHER INFORMATION: Chr17: 7578182-7578298 amplicon of the TP53
      gene

<400> SEQUENCE: 25

| ccccagttgc aaaccagacc tcaggcggct catagggcac caccacacta tgtcgaaaag | 60 |
| tgtttctgtc atccaaatac tccacacgca aatttccttc cactcggata agatgctgag | 120 |
| gaggggccag acctaagagc aatcagtgag gaatcagagg | 160 |

<210> SEQ ID NO 26
<211> LENGTH: 189
<212> TYPE: DNA
<213> ORGANISM: Artificial Sequence
<220> FEATURE:
<223> OTHER INFORMATION: Chr17: 7578389-7578537 amplicon of the TP53
      gene

<400> SEQUENCE: 26
accatcgcta tctgagcagc gctcatggtg ggggcagcgc ctcacaacct ccgtcatgtg     60
ctgtgactgc ttgtagatgg ccatggcgcg gacgcgggtg ccgggcgggg gtgtggaatc    120
aacccacagc tgcacagggc aggtcttggc cagttggcaa acatcttgt tgagggcagg    180 ggagtactg                                                            189

<210> SEQ ID NO 27
<211> LENGTH: 19
<212> TYPE: DNA
<213> ORGANISM: Artificial Sequence
<220> FEATURE:
<223> OTHER INFORMATION: ALK primer

<400> SEQUENCE: 27
actgcctctt gacctgtcc                                                  19

<210> SEQ ID NO 28
<211> LENGTH: 20
<212> TYPE: DNA
<213> ORGANISM: Artificial Sequence
<220> FEATURE:
<223> OTHER INFORMATION: ALK primer

<400> SEQUENCE: 28
taagggacaa gcagccacac                                                 20

<210> SEQ ID NO 29
<211> LENGTH: 25
<212> TYPE: DNA
<213> ORGANISM: Artificial Sequence
<220> FEATURE:
<223> OTHER INFORMATION: ALK primer

<400> SEQUENCE: 29
ccagactcag ctcagttaat tttgg                                           25

<210> SEQ ID NO 30
<211> LENGTH: 19
<212> TYPE: DNA
<213> ORGANISM: Artificial Sequence
<220> FEATURE:
<223> OTHER INFORMATION: ALK primer

<400> SEQUENCE: 30
cggaggaagg acttgaggt                                                  19

<210> SEQ ID NO 31
<211> LENGTH: 29
<212> TYPE: DNA
<213> ORGANISM: Artificial Sequence
<220> FEATURE:
<223> OTHER INFORMATION: BRAF primer

<400> SEQUENCE: 31
ctactgtttt cctttactta ctacacctc                                       29

<210> SEQ ID NO 32
<211> LENGTH: 27
<212> TYPE: DNA
<213> ORGANISM: Artificial Sequence
<220> FEATURE:
<223> OTHER INFORMATION: BRAF primer

<400> SEQUENCE: 32
cctcaattct taccatccac aaaatgg                                27

<210> SEQ ID NO 33
<211> LENGTH: 23
<212> TYPE: DNA
<213> ORGANISM: Artificial Sequence
<220> FEATURE:
<223> OTHER INFORMATION: EGFR primer

<400> SEQUENCE: 33
tgacccttgt ctctgtgttc ttg                                    23

<210> SEQ ID NO 34
<211> LENGTH: 23
<212> TYPE: DNA
<213> ORGANISM: Artificial Sequence
<220> FEATURE:
<223> OTHER INFORMATION: BRAF primer

<400> SEQUENCE: 34
ccagggacct taccttatac acc                                    23

<210> SEQ ID NO 35
<211> LENGTH: 23
<212> TYPE: DNA
<213> ORGANISM: Artificial Sequence
<220> FEATURE:
<223> OTHER INFORMATION: EGFR primer

<400> SEQUENCE: 35
acaattgcca gttaacgtct tcc                                    23

<210> SEQ ID NO 36
<211> LENGTH: 22
<212> TYPE: DNA
<213> ORGANISM: Artificial Sequence
<220> FEATURE:
<223> OTHER INFORMATION: EGFR primer

<400> SEQUENCE: 36
acacagcaaa gcagaaactc ac                                     22

<210> SEQ ID NO 37
<211> LENGTH: 18
<212> TYPE: DNA
<213> ORGANISM: Artificial Sequence
<220> FEATURE:
<223> OTHER INFORMATION: EGFR primer

<400> SEQUENCE: 37
gaagccacac tgacgtgc                                          18

<210> SEQ ID NO 38
<211> LENGTH: 21
<212> TYPE: DNA
<213> ORGANISM: Artificial Sequence
<220> FEATURE:

```
<223> OTHER INFORMATION: EGFR primer

<400> SEQUENCE: 38
gtgttcccgg acatagtcca g                                              21

<210> SEQ ID NO 39
<211> LENGTH: 21
<212> TYPE: DNA
<213> ORGANISM: Artificial Sequence
<220> FEATURE:
<223> OTHER INFORMATION: EGFR primer

<400> SEQUENCE: 39
ccgcagcatg tcaagatcac a                                              21

<210> SEQ ID NO 40
<211> LENGTH: 25
<212> TYPE: DNA
<213> ORGANISM: Artificial Sequence
<220> FEATURE:
<223> OTHER INFORMATION: EGFR primer

<400> SEQUENCE: 40
taaacaatac agctagtggg aaggc                                          25

<210> SEQ ID NO 41
<211> LENGTH: 20
<212> TYPE: DNA
<213> ORGANISM: Artificial Sequence
<220> FEATURE:
<223> OTHER INFORMATION: ERBB2 primer

<400> SEQUENCE: 41 catccctct cagcgtaccc                                                 20

<210> SEQ ID NO 42
<211> LENGTH: 21
<212> TYPE: DNA
<213> ORGANISM: Artificial Sequence
<220> FEATURE:
<223> OTHER INFORMATION: ERBB2 primer

<400> SEQUENCE: 42
cggacatggt ctaagaggca g                                              21

<210> SEQ ID NO 43
<211> LENGTH: 25
<212> TYPE: DNA
<213> ORGANISM: Artificial Sequence
<220> FEATURE:
<223> OTHER INFORMATION: KRAS primer

<400> SEQUENCE: 43
tgcactgtaa taatccagac tgtgt                                          25

<210> SEQ ID NO 44
<211> LENGTH: 22
<212> TYPE: DNA
<213> ORGANISM: Artificial Sequence
<220> FEATURE:
<223> OTHER INFORMATION: KRAS primer

<400> SEQUENCE: 44
agtcctcatg tactggtccc tc                                             22
```

```
<210> SEQ ID NO 45
<211> LENGTH: 22
<212> TYPE: DNA
<213> ORGANISM: Artificial Sequence
<220> FEATURE:
<223> OTHER INFORMATION: KRAS primer

<400> SEQUENCE: 45
aaggcctgct gaaaatgact ga                                              22

<210> SEQ ID NO 46
<211> LENGTH: 22
<212> TYPE: DNA
<213> ORGANISM: Artificial Sequence
<220> FEATURE:
<223> OTHER INFORMATION: KRAS primer

<400> SEQUENCE: 46
aaagaatggt cctgcaccag ta                                              22

<210> SEQ ID NO 47
<211> LENGTH: 21
<212> TYPE: DNA
<213> ORGANISM: Artificial Sequence
<220> FEATURE:
<223> OTHER INFORMATION: MET primer

<400> SEQUENCE: 47
tcgatctgcc atgtgtgcat t                                               21

<210> SEQ ID NO 48
<211> LENGTH: 22
<212> TYPE: DNA
<213> ORGANISM: Artificial Sequence
<220> FEATURE:
<223> OTHER INFORMATION: MET primer

<400> SEQUENCE: 48
gggaactgat gtgacttacc ct                                              22

<210> SEQ ID NO 49
<211> LENGTH: 24
<212> TYPE: DNA
<213> ORGANISM: Artificial Sequence
<220> FEATURE:
<223> OTHER INFORMATION: MET primer

<400> SEQUENCE: 49
ccatgatagc cgtctttaac aagc                                            24

<210> SEQ ID NO 50
<211> LENGTH: 25
<212> TYPE: DNA
<213> ORGANISM: Artificial Sequence
<220> FEATURE:
<223> OTHER INFORMATION: MET primer

<400> SEQUENCE: 50
agctcggtag tctacagatt cattt                                           25

<210> SEQ ID NO 51
<211> LENGTH: 22
<212> TYPE: DNA
<213> ORGANISM: Artificial Sequence
<220> FEATURE:
<223> OTHER INFORMATION: MET primer
```

```
<400> SEQUENCE: 51
atgttacgca gtgctaacca ag                                              22

<210> SEQ ID NO 52
<211> LENGTH: 26
<212> TYPE: DNA
<213> ORGANISM: Artificial Sequence
<220> FEATURE:
<223> OTHER INFORMATION: MET primer

<400> SEQUENCE: 52
gttgcaaacc acaaaagtat actcca                                          26

<210> SEQ ID NO 53
<211> LENGTH: 24
<212> TYPE: DNA
<213> ORGANISM: Artificial Sequence
<220> FEATURE:
<223> OTHER INFORMATION: MET primer

<400> SEQUENCE: 53
cagtcaaggt tgctgatttt ggtc                                            24

<210> SEQ ID NO 54
<211> LENGTH: 24
<212> TYPE: DNA
<213> ORGANISM: Artificial Sequence
<220> FEATURE:
<223> OTHER INFORMATION: MET primer

<400> SEQUENCE: 54
cacatctgac ttggtggtaa actt                                            24

<210> SEQ ID NO 55
<211> LENGTH: 24
<212> TYPE: DNA
<213> ORGANISM: Artificial Sequence
<220> FEATURE:
<223> OTHER INFORMATION: NRAS primer

<400> SEQUENCE: 55 caccccagg attcttacag aaaa                                             24

<210> SEQ ID NO 56
<211> LENGTH: 22
<212> TYPE: DNA
<213> ORGANISM: Artificial Sequence
<220> FEATURE:
<223> OTHER INFORMATION: NRAS primer

<400> SEQUENCE: 56
ttcgcctgtc ctcatgtatt gg                                              22

<210> SEQ ID NO 57
<211> LENGTH: 22
<212> TYPE: DNA
<213> ORGANISM: Artificial Sequence
<220> FEATURE:
<223> OTHER INFORMATION: NRAS primer

<400> SEQUENCE: 57
ctgagtacaa actggtggtg gt                                              22

<210> SEQ ID NO 58
<211> LENGTH: 22
```

<212> TYPE: DNA
<213> ORGANISM: Artificial Sequence
<220> FEATURE:
<223> OTHER INFORMATION: NRAS primer

<400> SEQUENCE: 58
tgagagacag gatcaggtca gc                                          22

<210> SEQ ID NO 59
<211> LENGTH: 26
<212> TYPE: DNA
<213> ORGANISM: Artificial Sequence
<220> FEATURE:
<223> OTHER INFORMATION: PIK3CA primer

<400> SEQUENCE: 59
ggaaaatgac aaagaacagc tcaaag                                      26

<210> SEQ ID NO 60
<211> LENGTH: 24
<212> TYPE: DNA
<213> ORGANISM: Artificial Sequence
<220> FEATURE:
<223> OTHER INFORMATION: PIK3CA primer

<400> SEQUENCE: 60
aacatgctga gatcagccaa attc                                        24

<210> SEQ ID NO 61
<211> LENGTH: 27
<212> TYPE: DNA
<213> ORGANISM: Artificial Sequence
<220> FEATURE:
<223> OTHER INFORMATION: PIK3CA primer

<400> SEQUENCE: 61
atgccagaac tacaatcttt tgatgac                                     27

<210> SEQ ID NO 62
<211> LENGTH: 23
<212> TYPE: DNA
<213> ORGANISM: Artificial Sequence
<220> FEATURE:
<223> OTHER INFORMATION: PIK3CA primer

<400> SEQUENCE: 62
caatccattt tgttgtcca gcc                                          23

<210> SEQ ID NO 63
<211> LENGTH: 29
<212> TYPE: DNA
<213> ORGANISM: Artificial Sequence
<220> FEATURE:
<223> OTHER INFORMATION: TP53 primer

<400> SEQUENCE: 63
ctcttttcct atcctgagta gtggtaatc                                   29

<210> SEQ ID NO 64
<211> LENGTH: 22
<212> TYPE: DNA
<213> ORGANISM: Artificial Sequence
<220> FEATURE:
<223> OTHER INFORMATION: TP53 primer

<400> SEQUENCE: 64
cttcttgtcc tgcttgctta cc                                              22

<210> SEQ ID NO 65
<211> LENGTH: 24
<212> TYPE: DNA
<213> ORGANISM: Artificial Sequence
<220> FEATURE:
<223> OTHER INFORMATION: TP53 primer

<400> SEQUENCE: 65
tcttgggcct gtgttatctc ctag                                            24

<210> SEQ ID NO 66
<211> LENGTH: 19
<212> TYPE: DNA
<213> ORGANISM: Artificial Sequence
<220> FEATURE:
<223> OTHER INFORMATION: TP53 primer

<400> SEQUENCE: 66
gcaagtggct cctgacctg                                                  19

<210> SEQ ID NO 67
<211> LENGTH: 24
<212> TYPE: DNA
<213> ORGANISM: Artificial Sequence
<220> FEATURE:
<223> OTHER INFORMATION: TP53 primer

<400> SEQUENCE: 67
cctctgattc ctcactgatt gctc                                            24

<210> SEQ ID NO 68
<211> LENGTH: 19
<212> TYPE: DNA
<213> ORGANISM: Artificial Sequence
<220> FEATURE:
<223> OTHER INFORMATION: TP53 primer

<400> SEQUENCE: 68
ccccagttgc aaaccagac                                                  19

<210> SEQ ID NO 69
<211> LENGTH: 20
<212> TYPE: DNA
<213> ORGANISM: Artificial Sequence
<220> FEATURE:
<223> OTHER INFORMATION: TP53 primer

<400> SEQUENCE: 69
cagtactccc ctgccctcaa                                                 20

<210> SEQ ID NO 70
<211> LENGTH: 20
<212> TYPE: DNA
<213> ORGANISM: Artificial Sequence
<220> FEATURE:
<223> OTHER INFORMATION: TP53 primer

<400> SEQUENCE: 70
accatcgcta tctgagcagc                                                 20

<210> SEQ ID NO 71
<211> LENGTH: 37
<212> TYPE: DNA
<213> ORGANISM: Artificial Sequence

```
<220> FEATURE:
<223> OTHER INFORMATION: pspf-1 primer

<400> SEQUENCE: 71
ggcatacgtc ctcgtctaac tgcctcttga cctgtcc                                    37

<210> SEQ ID NO 72
<211> LENGTH: 43
<212> TYPE: DNA
<213> ORGANISM: Artificial Sequence
<220> FEATURE:
<223> OTHER INFORMATION: pspf-2 primer

<400> SEQUENCE: 72
ggcatacgtc ctcgtctacc agactcagct cagttaattt tgg                             43

<210> SEQ ID NO 73
<211> LENGTH: 47
<212> TYPE: DNA
<213> ORGANISM: Artificial Sequence
<220> FEATURE:
<223> OTHER INFORMATION: pspf-3 primer

<400> SEQUENCE: 73
ggcatacgtc ctcgtctact actgttttcc tttacttact acacctc                         47

<210> SEQ ID NO 74
<211> LENGTH: 41
<212> TYPE: DNA
<213> ORGANISM: Artificial Sequence
<220> FEATURE:
<223> OTHER INFORMATION: pspf-4 primer

<400> SEQUENCE: 74
ggcatacgtc ctcgtctatg accttgtct ctgtgttctt g                                41

<210> SEQ ID NO 75
<211> LENGTH: 41
<212> TYPE: DNA
<213> ORGANISM: Artificial Sequence
<220> FEATURE:
<223> OTHER INFORMATION: pspf-5 primer

<400> SEQUENCE: 75
ggcatacgtc ctcgtctaac aattgccagt taacgtcttc c                               41

<210> SEQ ID NO 76
<211> LENGTH: 36
<212> TYPE: DNA
<213> ORGANISM: Artificial Sequence
<220> FEATURE:
<223> OTHER INFORMATION: pspf-6 primer

<400> SEQUENCE: 76
ggcatacgtc ctcgtctaga agccacactg acgtgc                                     36

<210> SEQ ID NO 77
<211> LENGTH: 39
<212> TYPE: DNA
<213> ORGANISM: Artificial Sequence
<220> FEATURE:
<223> OTHER INFORMATION: pspf-7 primer

<400> SEQUENCE: 77
ggcatacgtc ctcgtctacc gcagcatgtc aagatcaca                                  39
```

<210> SEQ ID NO 78
<211> LENGTH: 38
<212> TYPE: DNA
<213> ORGANISM: Artificial Sequence
<220> FEATURE:
<223> OTHER INFORMATION: pspf-8 primer

<400> SEQUENCE: 78
ggcatacgtc ctcgtctaca taccctctca gcgtaccc                                38

<210> SEQ ID NO 79
<211> LENGTH: 43
<212> TYPE: DNA
<213> ORGANISM: Artificial Sequence
<220> FEATURE:
<223> OTHER INFORMATION: pspf-9 primer

<400> SEQUENCE: 79
ggcatacgtc ctcgtctatg cactgtaata atccagactg tgt                          43

<210> SEQ ID NO 80
<211> LENGTH: 40
<212> TYPE: DNA
<213> ORGANISM: Artificial Sequence
<220> FEATURE:
<223> OTHER INFORMATION: pspf-10 primer

<400> SEQUENCE: 80
ggcatacgtc ctcgtctaaa ggcctgctga aaatgactga                              40

<210> SEQ ID NO 81
<211> LENGTH: 39
<212> TYPE: DNA
<213> ORGANISM: Artificial Sequence
<220> FEATURE:
<223> OTHER INFORMATION: pspf-11 primer

<400> SEQUENCE: 81
ggcatacgtc ctcgtctatc gatctgccat gtgtgcatt                               39

<210> SEQ ID NO 82
<211> LENGTH: 42
<212> TYPE: DNA
<213> ORGANISM: Artificial Sequence
<220> FEATURE:
<223> OTHER INFORMATION: pspf-12 primer

<400> SEQUENCE: 82
ggcatacgtc ctcgtctacc atgatagccg tctttaacaa gc                           42

<210> SEQ ID NO 83
<211> LENGTH: 40
<212> TYPE: DNA
<213> ORGANISM: Artificial Sequence
<220> FEATURE:
<223> OTHER INFORMATION: pspf-13 primer

<400> SEQUENCE: 83
ggcatacgtc ctcgtctaat gttacgcagt gctaaccaag                              40

<210> SEQ ID NO 84
<211> LENGTH: 42
<212> TYPE: DNA
<213> ORGANISM: Artificial Sequence
<220> FEATURE:
<223> OTHER INFORMATION: pspf-14 primer

<400> SEQUENCE: 84
ggcatacgtc ctcgtctaca gtcaaggttg ctgattttgg tc                42

<210> SEQ ID NO 85
<211> LENGTH: 42
<212> TYPE: DNA
<213> ORGANISM: Artificial Sequence
<220> FEATURE:
<223> OTHER INFORMATION: pspf-15 primer

<400> SEQUENCE: 85
ggcatacgtc ctcgtctaca cccccaggat tcttacagaa aa                42

<210> SEQ ID NO 86
<211> LENGTH: 40
<212> TYPE: DNA
<213> ORGANISM: Artificial Sequence
<220> FEATURE:
<223> OTHER INFORMATION: pspf-16 primer

<400> SEQUENCE: 86
ggcatacgtc ctcgtctact gagtacaaac tggtggtggt                   40

<210> SEQ ID NO 87
<211> LENGTH: 44
<212> TYPE: DNA
<213> ORGANISM: Artificial Sequence
<220> FEATURE:
<223> OTHER INFORMATION: pspf-17 primer

<400> SEQUENCE: 87
ggcatacgtc ctcgtctagg aaaatgacaa agaacagctc aaag              44

<210> SEQ ID NO 88
<211> LENGTH: 45
<212> TYPE: DNA
<213> ORGANISM: Artificial Sequence
<220> FEATURE:
<223> OTHER INFORMATION: pspf-18 primer

<400> SEQUENCE: 88
ggcatacgtc ctcgtctaat gccagaacta caatcttttg atgac             45

<210> SEQ ID NO 89
<211> LENGTH: 47
<212> TYPE: DNA
<213> ORGANISM: Artificial Sequence
<220> FEATURE:
<223> OTHER INFORMATION: pspf-19 primer

<400> SEQUENCE: 89
ggcatacgtc ctcgtctact cttttcctat cctgagtagt ggtaatc           47

<210> SEQ ID NO 90
<211> LENGTH: 42
<212> TYPE: DNA
<213> ORGANISM: Artificial Sequence
<220> FEATURE:
<223> OTHER INFORMATION: pspf-20 primer

<400> SEQUENCE: 90
ggcatacgtc ctcgtctatc ttgggcctgt gttatctcct ag                42

<210> SEQ ID NO 91

<210> SEQ ID NO 91
<211> LENGTH: 42
<212> TYPE: DNA
<213> ORGANISM: Artificial Sequence
<220> FEATURE:
<223> OTHER INFORMATION: pspf-21 primer

<400> SEQUENCE: 91
ggcatacgtc ctcgtctacc tctgattcct cactgattgc tc            42

<210> SEQ ID NO 92
<211> LENGTH: 38
<212> TYPE: DNA
<213> ORGANISM: Artificial Sequence
<220> FEATURE:
<223> OTHER INFORMATION: pspf-22 primer

<400> SEQUENCE: 92
ggcatacgtc ctcgtctaca gtactcccct gccctcaa                 38

<210> SEQ ID NO 93
<211> LENGTH: 39
<212> TYPE: DNA
<213> ORGANISM: Artificial Sequence
<220> FEATURE:
<223> OTHER INFORMATION: pspr-1 primer

<400> SEQUENCE: 93
tctatgggca gtcggtgatt aagggacaag cagccacac                39

<210> SEQ ID NO 94
<211> LENGTH: 38
<212> TYPE: DNA
<213> ORGANISM: Artificial Sequence
<220> FEATURE:
<223> OTHER INFORMATION: pspr-2 primer

<400> SEQUENCE: 94
tctatgggca gtcggtgatc ggaggaagga cttgaggt                 38

<210> SEQ ID NO 95
<211> LENGTH: 46
<212> TYPE: DNA
<213> ORGANISM: Artificial Sequence
<220> FEATURE:
<223> OTHER INFORMATION: pspr-3 primer

<400> SEQUENCE: 95
tctatgggca gtcggtgatc ctcaattctt accatccaca aaatgg        46

<210> SEQ ID NO 96
<211> LENGTH: 42
<212> TYPE: DNA
<213> ORGANISM: Artificial Sequence
<220> FEATURE:
<223> OTHER INFORMATION: pspr-4 primer

<400> SEQUENCE: 96
tctatgggca gtcggtgatc cagggacctt accttataca cc            42

<210> SEQ ID NO 97
<211> LENGTH: 41
<212> TYPE: DNA
<213> ORGANISM: Artificial Sequence
<220> FEATURE:
<223> OTHER INFORMATION: pspr-5 primer

<400> SEQUENCE: 97
tctatgggca gtcggtgata cacagcaaag cagaaactca c           41

<210> SEQ ID NO 98
<211> LENGTH: 40
<212> TYPE: DNA
<213> ORGANISM: Artificial Sequence
<220> FEATURE:
<223> OTHER INFORMATION: pspr-6 primer

<400> SEQUENCE: 98
tctatgggca gtcggtgatg tgttcccgga catagtccag            40

<210> SEQ ID NO 99
<211> LENGTH: 44
<212> TYPE: DNA
<213> ORGANISM: Artificial Sequence
<220> FEATURE:
<223> OTHER INFORMATION: pspr-7 primer

<400> SEQUENCE: 99
tctatgggca gtcggtgatt aaacaataca gctagtggga aggc       44

<210> SEQ ID NO 100
<211> LENGTH: 40
<212> TYPE: DNA
<213> ORGANISM: Artificial Sequence
<220> FEATURE:
<223> OTHER INFORMATION: pspr-8 primer

<400> SEQUENCE: 100
tctatgggca gtcggtgatc ggacatggtc taagaggcag            40

<210> SEQ ID NO 101
<211> LENGTH: 41
<212> TYPE: DNA
<213> ORGANISM: Artificial Sequence
<220> FEATURE:
<223> OTHER INFORMATION: pspr-9 primer

<400> SEQUENCE: 101
tctatgggca gtcggtgata gtcctcatgt actggtccct c          41

<210> SEQ ID NO 102
<211> LENGTH: 41
<212> TYPE: DNA
<213> ORGANISM: Artificial Sequence
<220> FEATURE:
<223> OTHER INFORMATION: pspr-10 primer

<400> SEQUENCE: 102
tctatgggca gtcggtgata aagaatggtc ctgcaccagt a          41

<210> SEQ ID NO 103
<211> LENGTH: 41
<212> TYPE: DNA
<213> ORGANISM: Artificial Sequence
<220> FEATURE:
<223> OTHER INFORMATION: pspr-11 primer

<400> SEQUENCE: 103
tctatgggca gtcggtgatg ggaactgatg tgacttaccc t          41

<210> SEQ ID NO 104
<211> LENGTH: 44
<212> TYPE: DNA

```
<213> ORGANISM: Artificial Sequence
<220> FEATURE:
<223> OTHER INFORMATION: pspr-12 primer

<400> SEQUENCE: 104
tctatgggca gtcggtgata gctcggtagt ctacagattc attt            44

<210> SEQ ID NO 105
<211> LENGTH: 45
<212> TYPE: DNA
<213> ORGANISM: Artificial Sequence
<220> FEATURE:
<223> OTHER INFORMATION: pspr-13 primer

<400> SEQUENCE: 105
tctatgggca gtcggtgatg ttgcaaacca caaaagtata ctcca           45

<210> SEQ ID NO 106
<211> LENGTH: 43
<212> TYPE: DNA
<213> ORGANISM: Artificial Sequence
<220> FEATURE:
<223> OTHER INFORMATION: pspr-14 primer

<400> SEQUENCE: 106
tctatgggca gtcggtgatc acatctgact tggtggtaaa ctt             43

<210> SEQ ID NO 107
<211> LENGTH: 41
<212> TYPE: DNA
<213> ORGANISM: Artificial Sequence
<220> FEATURE:
<223> OTHER INFORMATION: pspr-15 primer

<400> SEQUENCE: 107
tctatgggca gtcggtgatt tcgcctgtcc tcatgtattg g               41

<210> SEQ ID NO 108
<211> LENGTH: 41
<212> TYPE: DNA
<213> ORGANISM: Artificial Sequence
<220> FEATURE:
<223> OTHER INFORMATION: pspr-16 primer

<400> SEQUENCE: 108
tctatgggca gtcggtgatt gagagacagg atcaggtcag c               41

<210> SEQ ID NO 109
<211> LENGTH: 43
<212> TYPE: DNA
<213> ORGANISM: Artificial Sequence
<220> FEATURE:
<223> OTHER INFORMATION: pspr-17 primer

<400> SEQUENCE: 109
tctatgggca gtcggtgata acatgctgag atcagccaaa ttc             43

<210> SEQ ID NO 110
<211> LENGTH: 42
<212> TYPE: DNA
<213> ORGANISM: Artificial Sequence
<220> FEATURE:
<223> OTHER INFORMATION: pspr-18 primer

<400> SEQUENCE: 110
tctatgggca gtcggtgatc aatccatttt tgttgtccag cc              42
```

<210> SEQ ID NO 111
<211> LENGTH: 41
<212> TYPE: DNA
<213> ORGANISM: Artificial Sequence
<220> FEATURE:
<223> OTHER INFORMATION: pspr-19 primer

<400> SEQUENCE: 111
tctatgggca gtcggtgatc ttcttgtcct gcttgcttac c                41

<210> SEQ ID NO 112
<211> LENGTH: 38
<212> TYPE: DNA
<213> ORGANISM: Artificial Sequence
<220> FEATURE:
<223> OTHER INFORMATION: pspr-20 primer

<400> SEQUENCE: 112
tctatgggca gtcggtgatg caagtggctc ctgacctg                    38

<210> SEQ ID NO 113
<211> LENGTH: 38
<212> TYPE: DNA
<213> ORGANISM: Artificial Sequence
<220> FEATURE:
<223> OTHER INFORMATION: pspr-21 primer

<400> SEQUENCE: 113
tctatgggca gtcggtgatc cccagttgca aaccagac                    38

<210> SEQ ID NO 114
<211> LENGTH: 39
<212> TYPE: DNA
<213> ORGANISM: Artificial Sequence
<220> FEATURE:
<223> OTHER INFORMATION: pspr-22 primer

<400> SEQUENCE: 114
tctatgggca gtcggtgata ccatcgctat ctgagcagc                   39

<210> SEQ ID NO 115
<211> LENGTH: 59
<212> TYPE: DNA
<213> ORGANISM: Artificial Sequence
<220> FEATURE:
<223> OTHER INFORMATION: puf-1 primer

<400> SEQUENCE: 115
ccatctcatc cctgcgtgtc tccgactcag cttgacaccg cggcatacgt cctcgtcta    59

<210> SEQ ID NO 116
<211> LENGTH: 60
<212> TYPE: DNA
<213> ORGANISM: Artificial Sequence
<220> FEATURE:
<223> OTHER INFORMATION: puf-2 primer

<400> SEQUENCE: 116
ccatctcatc cctgcgtgtc tccgactcag ttggaggcca gcggcatacg tcctcgtcta   60

<210> SEQ ID NO 117
<211> LENGTH: 60
<212> TYPE: DNA
<213> ORGANISM: Artificial Sequence
<220> FEATURE:

<223> OTHER INFORMATION: puf-3 primer

<400> SEQUENCE: 117
ccatctcatc cctgcgtgtc tccgactcag tggagcttcc tcggcatacg tcctcgtcta    60

<210> SEQ ID NO 118
<211> LENGTH: 59
<212> TYPE: DNA
<213> ORGANISM: Artificial Sequence
<220> FEATURE:
<223> OTHER INFORMATION: puf-4 primer

<400> SEQUENCE: 118
ccatctcatc cctgcgtgtc tccgactcag tcagtccgaa cggcatacgt cctcgtcta     59

<210> SEQ ID NO 119
<211> LENGTH: 60
<212> TYPE: DNA
<213> ORGANISM: Artificial Sequence
<220> FEATURE:
<223> OTHER INFORMATION: puf-5 primer

<400> SEQUENCE: 119
ccatctcatc cctgcgtgtc tccgactcag taaggcaacc acggcatacg tcctcgtcta    60

<210> SEQ ID NO 120
<211> LENGTH: 59
<212> TYPE: DNA
<213> ORGANISM: Artificial Sequence
<220> FEATURE:
<223> OTHER INFORMATION: puf-6 primer

<400> SEQUENCE: 120
ccatctcatc cctgcgtgtc tccgactcag ttctaagaga cggcatacgt cctcgtcta     59

<210> SEQ ID NO 121
<211> LENGTH: 60
<212> TYPE: DNA
<213> ORGANISM: Artificial Sequence
<220> FEATURE:
<223> OTHER INFORMATION: puf-7 primer

<400> SEQUENCE: 121
ccatctcatc cctgcgtgtc tccgactcag tcctaacata acggcatacg tcctcgtcta    60

<210> SEQ ID NO 122
<211> LENGTH: 59
<212> TYPE: DNA
<213> ORGANISM: Artificial Sequence
<220> FEATURE:
<223> OTHER INFORMATION: puf-8 primer

<400> SEQUENCE: 122
ccatctcatc cctgcgtgtc tccgactcag cggacaatgg cggcatacgt cctcgtcta     59

<210> SEQ ID NO 123
<211> LENGTH: 60
<212> TYPE: DNA
<213> ORGANISM: Artificial Sequence
<220> FEATURE:
<223> OTHER INFORMATION: puf-9 primer

<400> SEQUENCE: 123
ccatctcatc cctgcgtgtc tccgactcag ttgagcctat tcggcatacg tcctcgtcta    60

```
<210> SEQ ID NO 124
<211> LENGTH: 59
<212> TYPE: DNA
<213> ORGANISM: Artificial Sequence
<220> FEATURE:
<223> OTHER INFORMATION: puf-10 primer

<400> SEQUENCE: 124
ccatctcatc cctgcgtgtc tccgactcag ccgcatggaa cggcatacgt cctcgtcta      59

<210> SEQ ID NO 125
<211> LENGTH: 41
<212> TYPE: DNA
<213> ORGANISM: Artificial Sequence
<220> FEATURE:
<223> OTHER INFORMATION: pur primer

<400> SEQUENCE: 125
ccactacgcc tccgctttcc tctctatggg cagtcggtga t                         41
```